(12) United States Patent
Nachtrab et al.

(10) Patent No.: US 11,471,202 B2
(45) Date of Patent: Oct. 18, 2022

(54) JOINT OSTEOTOMY SYSTEM AND METHOD

(71) Applicant: Wright Medical Technology, Inc., Memphis, TN (US)

(72) Inventors: Dean J. Nachtrab, Memphis, TN (US); David G. Reynolds, Fairport, NY (US); Paul M. Stemniski, Arlington, TN (US); Julia C. Alspaugh, Memphis, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 234 days.

(21) Appl. No.: 16/655,467

(22) Filed: Oct. 17, 2019

(65) Prior Publication Data
US 2020/0046412 A1   Feb. 13, 2020

Related U.S. Application Data

(63) Continuation of application No. PCT/US2017/044419, filed on Jul. 28, 2017.

(51) Int. Cl.
*A61B 17/16* (2006.01)
*A61B 17/17* (2006.01)
(Continued)

(52) U.S. Cl.
CPC .......... *A61B 17/8095* (2013.01); *A61B 17/15* (2013.01); *A61B 17/151* (2013.01);
(Continued)

(58) Field of Classification Search
CPC .. A61F 2/4202; A61F 2/4606; A61B 17/1682; A61B 17/1775; A61B 17/1674; A61B 17/1764
See application file for complete search history.

(56) References Cited

U.S. PATENT DOCUMENTS 4,566,448 A * 1/1986 Rohr, Jr. .............. A61B 17/155
606/88
5,540,696 A 7/1996 Booth, Jr. et al.
(Continued)

FOREIGN PATENT DOCUMENTS

CN 101790353 A 7/2010
EP 809969 A2 12/1997
(Continued)

OTHER PUBLICATIONS

First Examination Report issued in connection with corresponding Australian Patent Application No. 2020289764, dated Jun. 30, 2021, 3 pages.
(Continued)

*Primary Examiner* — Brian A Dukert
(74) *Attorney, Agent, or Firm* — Duane Morris LLP

(57) ABSTRACT

A system includes a first spacer sized and configured to be received within a resected bone space of a first bone and a second spacer sized and configured to be coupled to a second bone. The first spacer and the second spacer each include a body extending between a bone contacting surface and a coupling surface. At least one shim is positioned between the first and second spacers. The shim includes a body extending between a first coupling surface and a second coupling surface. The first spacer, the second spacer, and the at least one shim position the first and second bones in a predetermined alignment. An adjustable guide including a guide adapter and a guide body is configured to couple to the first spacer and is adjustable on a first axis.

16 Claims, 40 Drawing Sheets

(51) Int. Cl.
*A61B 17/80* (2006.01)
*A61B 17/15* (2006.01)
*A61B 17/88* (2006.01)
*A61F 2/30* (2006.01)
*A61F 2/42* (2006.01)
*A61B 17/68* (2006.01)
*A61F 2/46* (2006.01)
*A61B 34/10* (2016.01)
*A61B 17/00* (2006.01)

(52) U.S. Cl.
CPC .......... *A61B 17/1662* (2013.01); *A61B 17/17* (2013.01); *A61B 17/1775* (2016.11); *A61B 17/8897* (2013.01); *A61F 2/30724* (2013.01); *A61F 2/30734* (2013.01); *A61F 2/4202* (2013.01); *A61B 17/1682* (2013.01); *A61B 2017/00477* (2013.01); *A61B 2017/681* (2013.01); *A61B 2034/108* (2016.02); *A61F 2002/3055* (2013.01); *A61F 2002/3069* (2013.01); *A61F 2002/4205* (2013.01); *A61F 2002/4207* (2013.01); *A61F 2002/4615* (2013.01)

(56) References Cited

U.S. PATENT DOCUMENTS

| | | |
|---|---|---|
| 5,800,438 A | 9/1998 | Tuke et al. |
| 5,860,980 A | 1/1999 | Axelson, Jr. et al. |
| 5,911,723 A | 6/1999 | Ashby et al. |
| 6,022,377 A | 2/2000 | Nuelle et al. |
| 6,602,259 B1 | 8/2003 | Masini |
| 6,758,850 B2 | 7/2004 | Smith et al. |
| 7,011,687 B2 * | 3/2006 | Deffenbaugh ........ A61F 2/4202 623/21.18 |
| 7,104,997 B2 | 9/2006 | Lionberger et al. |
| 7,156,853 B2 | 1/2007 | Muratsu |
| 7,329,260 B2 | 2/2008 | Auger et al. |
| 7,455,647 B2 | 11/2008 | Tarabichi |
| 7,803,191 B2 | 9/2010 | Biedermann et al. |
| 7,837,691 B2 | 11/2010 | Cordes et al. |
| 8,083,746 B2 | 12/2011 | Novak |
| 8,137,361 B2 | 3/2012 | Duggineni et al. |
| 8,162,951 B2 | 4/2012 | Kaufman |
| 8,323,290 B2 | 12/2012 | Metzger et al. |
| 8,425,524 B2 | 4/2013 | Aker et al. |
| 8,562,617 B2 | 10/2013 | Chessar et al. |
| 8,603,095 B2 | 12/2013 | Haines et al. |
| 8,673,011 B2 | 3/2014 | Theofilos et al. |
| 8,734,454 B2 | 5/2014 | Disilvestro et al. |
| 8,771,365 B2 | 7/2014 | Bojarski et al. |
| 8,808,303 B2 | 11/2014 | Stemniski et al. |
| 9,005,207 B2 | 4/2015 | Dodds et al. |
| 9,050,197 B2 | 6/2015 | Lorio et al. |
| 9,066,804 B2 | 6/2015 | Haines et al. |
| 9,161,761 B2 | 10/2015 | Metzger et al. |
| 9,186,154 B2 | 11/2015 | Li |
| 9,402,640 B2 | 8/2016 | Reynolds et al. |
| 9,439,656 B2 | 9/2016 | Chana et al. |
| 9,592,133 B2 | 3/2017 | Toler et al. |
| 2003/0187452 A1 | 10/2003 | Smith et al. |
| 2004/0122441 A1 | 6/2004 | Muratsu |
| 2005/0038442 A1 | 2/2005 | Freeman |
| 2005/0273114 A1 | 12/2005 | Novak |
| 2006/0142870 A1 | 6/2006 | Robinson et al. |
| 2006/0189998 A1 | 8/2006 | Rasmussen |
| 2006/0241640 A1 | 10/2006 | Briard et al. |
| 2007/0233140 A1 | 10/2007 | Metzger et al. |
| 2009/0043309 A1 | 2/2009 | Rasmussen |
| 2009/0043310 A1 | 2/2009 | Rasmussen |
| 2010/0212138 A1 | 8/2010 | Carroll et al. |
| 2010/0305575 A1 | 12/2010 | Wilkinson et al. |
| 2011/0257654 A1 | 10/2011 | Haines et al. |
| 2012/0053591 A1 | 3/2012 | Haines et al. |
| 2012/0130434 A1 | 5/2012 | Stemniski et al. |
| 2012/0158152 A1 | 6/2012 | Claypool et al. |
| 2012/0271314 A1 | 10/2012 | Stemniski et al. |
| 2013/0197527 A1 | 8/2013 | Nadjadi et al. |
| 2013/0325014 A1 | 12/2013 | Sordelet et al. |
| 2014/0025081 A1 | 1/2014 | Lorio et al. |
| 2014/0228853 A1 | 8/2014 | Rock |
| 2015/0105782 A1 | 4/2015 | D'Lima et al. |
| 2015/0257899 A1 * | 9/2015 | Luna .................. A61B 17/1739 623/21.18 |
| 2016/0199077 A1 | 7/2016 | Dungy |
| 2016/0213384 A1 | 7/2016 | Fallin et al. |
| 2016/0361071 A1 | 12/2016 | Mohamed |

FOREIGN PATENT DOCUMENTS

| | | |
|---|---|---|
| EP | 2704648 A1 | 3/2014 |
| EP | 2753248 A1 | 7/2014 |
| JP | 2009525824 A | 7/2009 |
| JP | 2014530649 A | 11/2014 |
| JP | 2014239900 A | 12/2014 |
| JP | 2015180353 A | 10/2015 |
| JP | 5803013 B2 | 11/2015 |
| JP | 2017080569 A | 5/2017 |
| WO | 2006028971 A1 | 3/2006 |
| WO | 2010138836 A | 12/2010 |
| WO | 2012020460 A1 | 2/2012 |
| WO | 2016112092 A1 | 7/2016 |
| WO | 2016138913 A1 | 9/2016 |

OTHER PUBLICATIONS

First Examination Report issued in connection with corresponding Australian Patent Application No. 2017425028, dated Mar. 18, 2020, 3 pages.
European Search Report issued in connection with corresponding European Patent Application No. 17919404.8, dated Feb. 9, 2021, 16 pages.
First Japanese Office Action issued in connection with corresponding Japanese Patent Application No. 2021-026215, dated Feb. 1, 2022, 4 pages.
Partial European Search Report issued in connection with corresponding European Patent Application No. 17919404.8, dated Oct. 22, 2019, 15 pages.
Office Action issued in connection with corresponding Japanese Patent Application No. 2019-557442, dated Nov. 24, 2020, 7 pages.
Office Action issued in connection with corresponding Canadian Patent Application No. 3059895, dated Dec. 9, 2020, 3 pages.
International Search Report and Written Opinion issued in connection with corresponding International Patent Application No. PCT/US2017/044419, dated Apr. 26, 2018, 39 pages.
First Office Action issued in connection with corresponding Chinese Patent Application No. 2017800899442.2, dated Apr. 6, 2022, 8 pages.

* cited by examiner

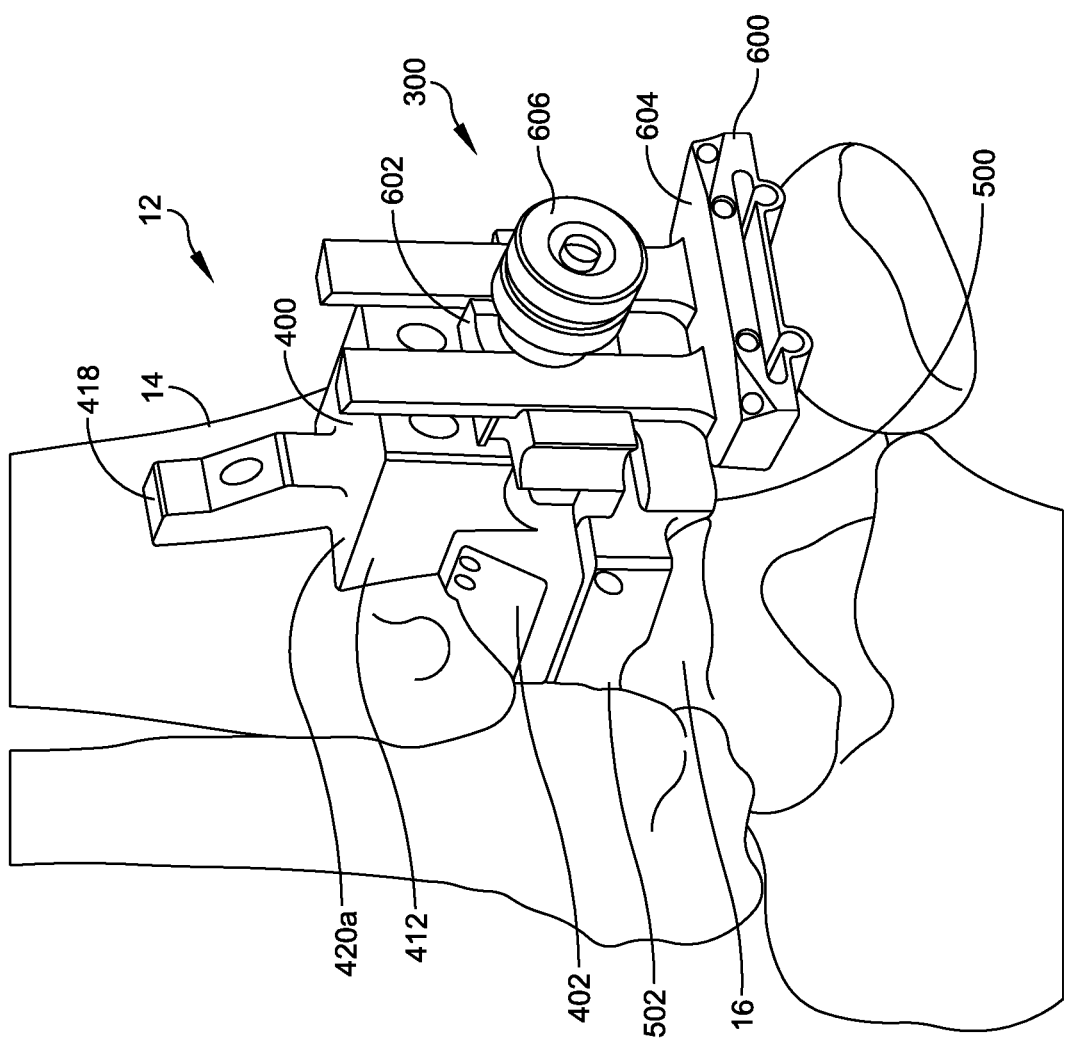

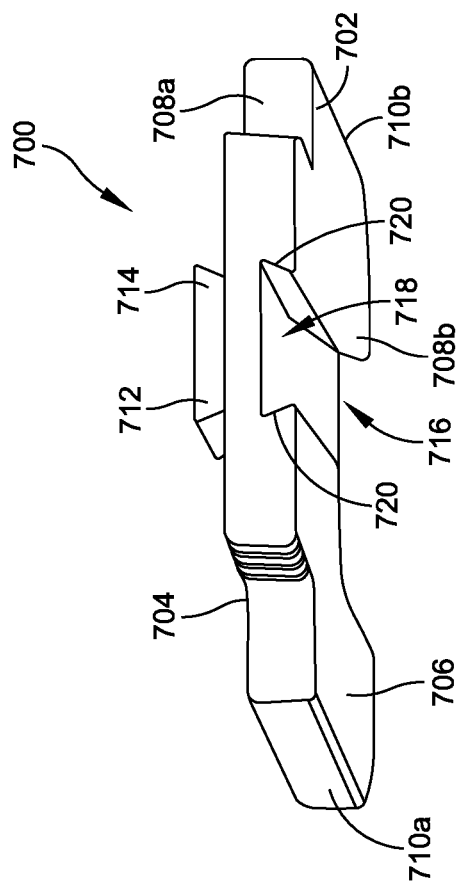
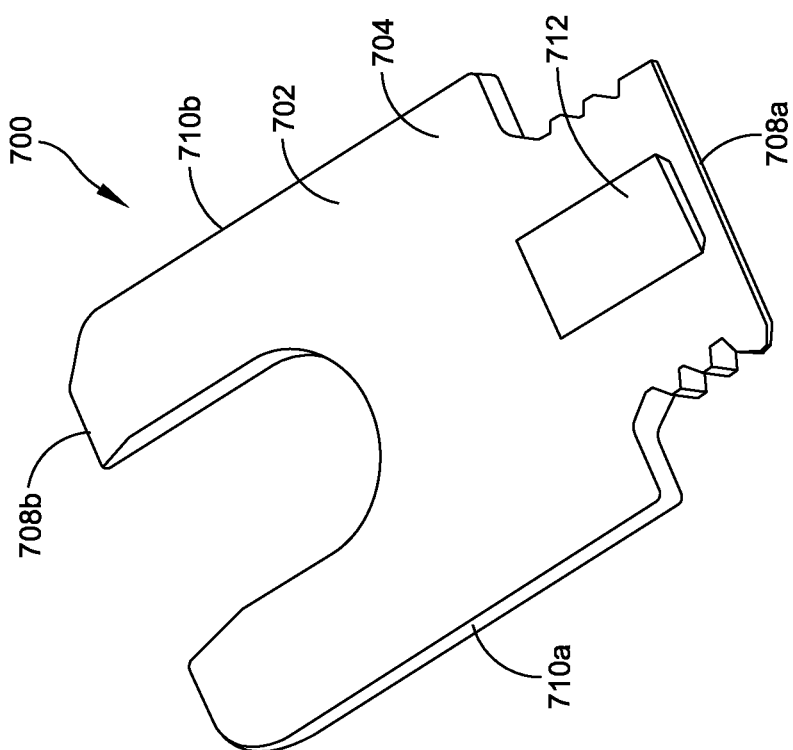
FIG. 16
FIG. 17

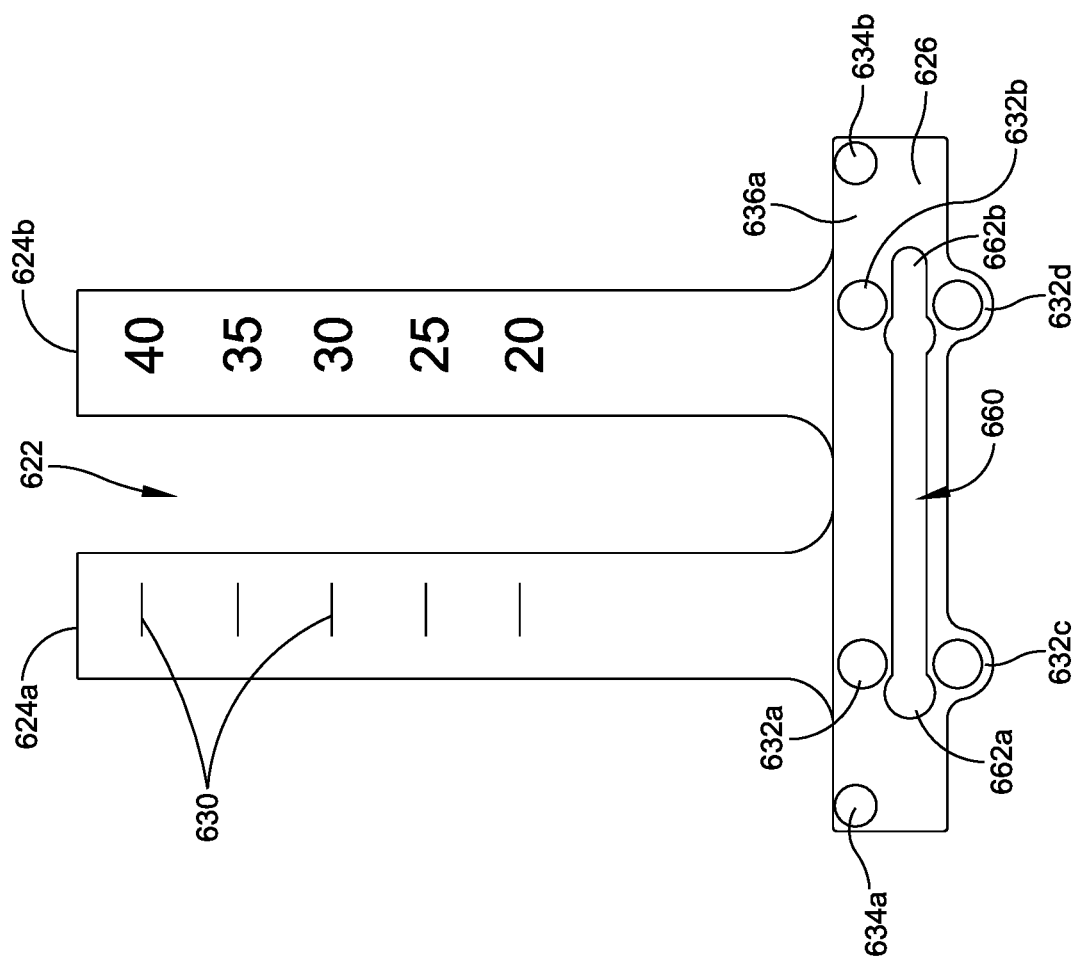

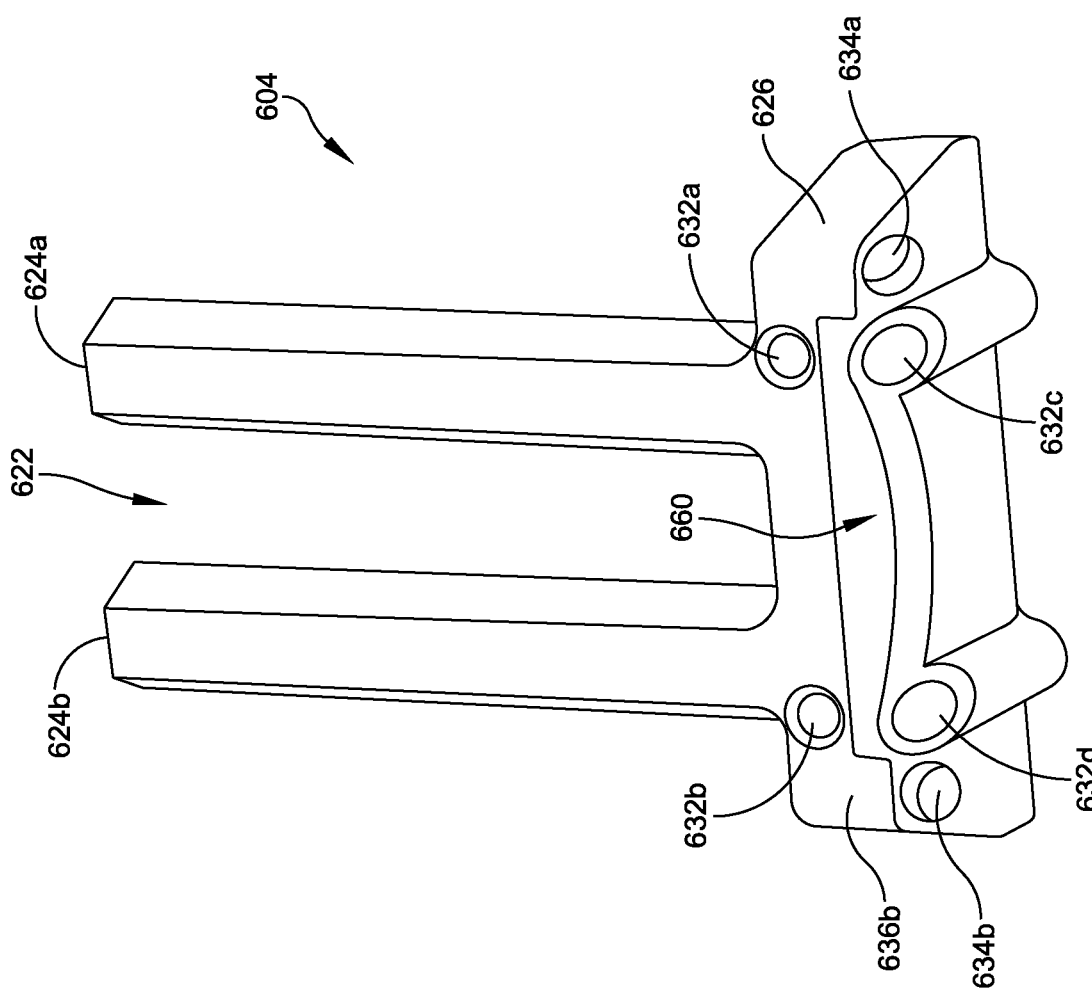

JOINT OSTEOTOMY SYSTEM AND METHOD

CROSS REFERENCE TO RELATED APPLICATION

This application is a continuation of International Patent Application No. PCT/US2017/044419, filed on Jul. 28, 2017, the entirety of which is incorporated by reference herein.

BACKGROUND

The ankle is a joint that acts much like a hinge. The joint is formed by the union of three bones. The ankle bone is the talus. The top of the talus fits inside a socket that is formed by the lower end of the tibia and the fibula, the small bone of the lower leg. Arthritis, bone degeneration, and/or injury can cause ankle joint deterioration resulting in pain, reduced range of motion, and decreased quality of life. In many cases, physicians are recommending ankle replacement surgery with an implant as an option.

A primary ankle replacement surgery can include replacement of portions of one or more of the bones of the ankle with one or more implants. The primary ankle replacement surgery can correct misalignments, deformities, and other issues of the ankle joint. In some cases, a revision surgery is necessary to correct additional deformities, misalignments, or other issues of the ankle joint not corrected during a primary ankle replacement surgery and/or that develop after the primary ankle replacement surgery.

SUMMARY

In various embodiments, a system includes a first spacer sized and configured to be received within a joint space of a first bone. The first spacer defines a body extending between a first surface and a second surface. The system further includes an adjustable guide includes a guide adapter and a guide body. The guide adapter is configured to couple the adjustable guide to the first spacer. The guide body is adjustable along a first axis with respect to the guide adapter.

In various embodiments, a system includes a first spacer sized and configured to be received within a joint space of a first bone. The first spacer defines a body extending between a first surface and a second surface. The system further includes at least one shim comprising a body extending between an upper surface and a lower surface. The upper surface is configured to couple the at least one shim to the second surface of the first spacer. The system also includes an adjustable guide comprising a guide adapter configured to be coupled the first spacer and a guide body. The guide body comprises a first leg and a second leg extending from the guide body and spaced apart to define a slot sized and configured to receive a coupling element extending from the guide adapter. The guide body is adjustable along a first axis with respect to the guide adapter.

In various embodiments, a method includes coupling a first spacer to a joint space of a first bone. The first spacer defines a body extending between a first surface and a second surface. The first surface is positioned in contact with the first bone. A second spacer is coupled to a second bone. The second spacer defines a body extending between a first surface and a second surface. The second surface of the first spacer is configured to abut the second surface of the second spacer to position the first bone and the second bone in a predetermined alignment. An adjustable guide is coupled to one of the first spacer or the second spacer.

In various embodiments, a system includes a first spacer sized and configured to be received within a joint space of a first bone, a second spacer sized and configured to be coupled to a second bone, and at least one shim comprising a body extending between an upper surface and a lower surface. The first spacer and the second spacer each include a body extending between a first surface and a second surface. the upper surface of the at least one shim is configured to couple the at least one shim to the second surface of the first spacer and the lower surface is configured to couple the at least one shim to the second surface of the second spacer. The first spacer, the second spacer, and the at least one shim are configured to position the first bone and the second bone in a predetermined alignment.

In various embodiments, a system includes a first spacer sized and configured to be received within a resected bone space of a first bone, a second spacer sized and configured to be coupled to a second bone, and at least one shim comprising a body extending between an upper surface and a lower surface. The first spacer and the second spacer each include a body extending between a first surface and a second surface. The first surface of the first spacer is configured to couple the first spacer to a lock detail of an implant coupled to the first bone. The upper surface of the at least one shim is configured to couple the at least one shim to the second surface of the first spacer and the lower surface is configured to couple the at least one shim to the second surface of the second spacer. The first spacer, the second spacer, and the at least one shim are configured to position the first bone and the second bone in a predetermined alignment.

In various embodiments, a method includes coupling a first spacer to a joint space of a first bone. The first spacer defines a body extending between a first surface and a second surface. The bone contacting surface is positioned in contact with the resected bone space. A second spacer is coupled to a second bone. The second spacer defines a body extending between a first surface and a second surface. An upper surface of a first shim is coupled to the second surface of the first spacer and a lower surface of the first shim is coupled to the second surface of the second spacer. The first spacer and the second spacer position the first bone and the second bone in a predetermined alignment. The first shim has a predetermined thickness configured to correct laxity between the first bone and the second bone.

In various embodiments, a system includes a first spacer sized and configured to be received within a joint space of a first bone and a second spacer sized and configured to be coupled to a second bone. The first spacer includes a body extending between a first surface and a second surface. The second surface defines an adjustment channel. The second spacer includes a body extending between a first surface and a second surface and an adjustment body extending from the second surface. The adjustment body is sized and configured to be inserted into the adjustment channel in a telescoping arrangement. The first spacer and the second spacer are configured to position the first bone and the second bone in a predetermined alignment.

In various embodiments, a method includes coupling a first spacer to a joint space of a first bone. The first spacer includes a body extending between a first surface and a second surface. The second surface defines an adjustment channel extending into the body. A second spacer is coupled to a second bone. The second spacer includes a body extending between a first surface and a second surface and an adjustment body extending from the second surface. The adjustment body is sized and configured to be inserted into the adjustment channel in a telescoping arrangement. The first spacer and the second spacer are configured to position the first bone and the second bone in a predetermined alignment. A spacing between the first spacer and the second spacer is adjusted by sliding the adjustment body within the adjustment channel. The spacing between the first spacer and the second spacer is configured to correct for laxity between the first bone and the second bone.

In various embodiments, a system includes a monolithic spacer having a body extending between a first surface and a second surface and an adjustable guide. The first surface is configured to abut a joint space of a first bone and the second surface includes a patient-specific topography matching a second bone. The adjustable guide includes a guide adapter configured to be coupled the monolithic spacer and a guide body defining a resection slot. The guide body comprises a first leg and a second leg extending from the guide body and spaced apart to define a slot sized and configured to receive a coupling element extending from the guide adapter.

In various embodiments, a system includes a body sized and configured to be receiving within a joint space and defining a tool path extending from a first side of the body to a second side of the body. The tool path is sized and configured to receive a surgical tool therethrough. A first bone engaging structure extends from the body in a first direction. The first bone engaging structure includes a first surface that is complementary to a surface topography of the bone. A drill guide is sized and configured to be received within tool path defined by the body. The drill guide defines an aperture sized and configured to receive the surgical tool therethrough. At least one shim is configured to be coupled to a bottom surface of the body. The shim includes a coupling element extending from an upper surface and the body defines a first complementary recess sized and configured to receive the coupling element therein.

In various embodiments, a system includes a first spacer sized and configured to be received within a joint space of a first bone and a first shim. The first spacer defines a body extending between a first surface and a second surface. The first shim includes a body extending between an upper surface and a lower surface. The upper surface is configured to couple the first shim to the second surface of the first spacer and the lower surface is configured to abut a second bone to position the first bone and the second bone in a predetermined alignment.

In various embodiments, a method includes positioning a first spacer within a joint space of a first bone and coupling a first shim to a surface of the first spacer. The first bone and a second bone are positioned in a predetermined alignment by abutting the first shim with the second bone.

BRIEF DESCRIPTION OF THE FIGURES

The features and advantages of the present invention will be more fully disclosed in, or rendered obvious by the following detailed description of the preferred embodiments, which are to be considered together with the accompanying drawings wherein like numbers refer to like parts and further wherein:

FIG. 6 illustrates a spacer assembly positioned between a first bone and a second bone of a joint, in accordance with some embodiments;

FIG. 16 illustrates an isometric view of a shim, in accordance with some embodiments;

FIG. 17 illustrates a bottom view of the shim of FIG. 16, in accordance with some embodiments;

FIG. 23 illustrates a front view of the resection guide of FIG. 22, in accordance with some embodiments;

FIG. 24 illustrates a rear isometric view of the resection guide of FIG. 22, in accordance with some embodiments;

DETAILED DESCRIPTION

Figure 1:
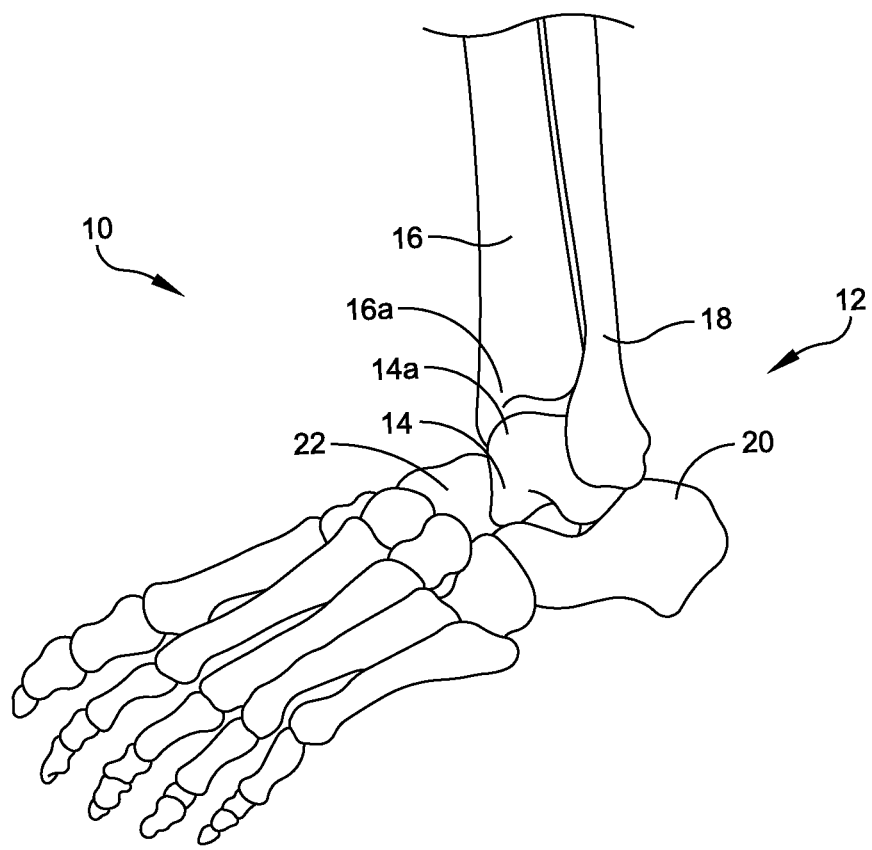
FIG. 1 illustrates the bones of a human foot and ankle.
Figure 2B:
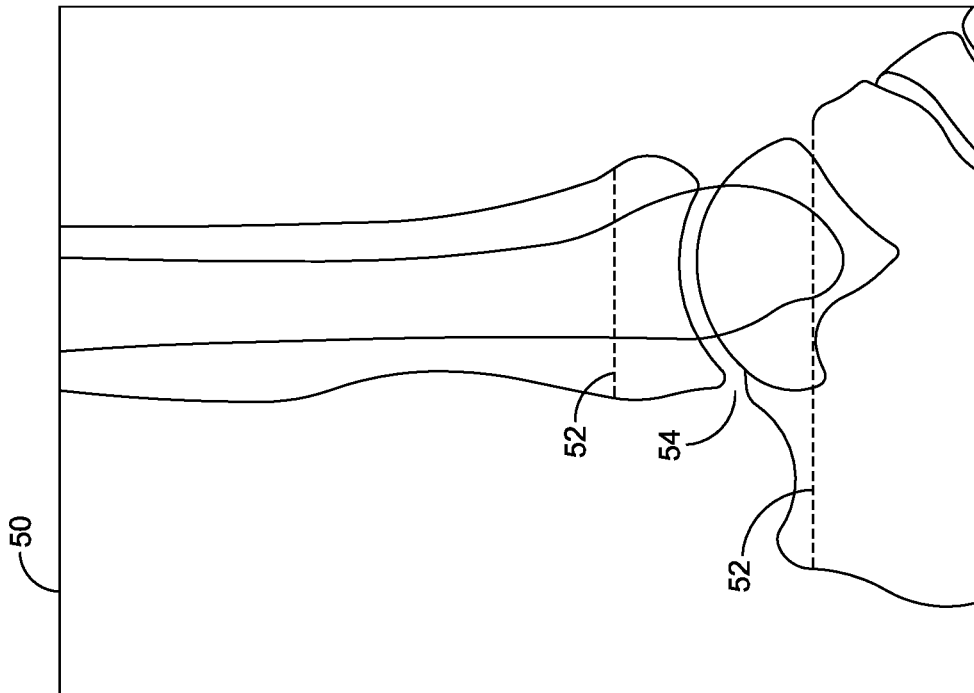
FIGS. 2A and 2B are schematic representations of a scanned image of a human foot and ankle joint.
Figure 2A:
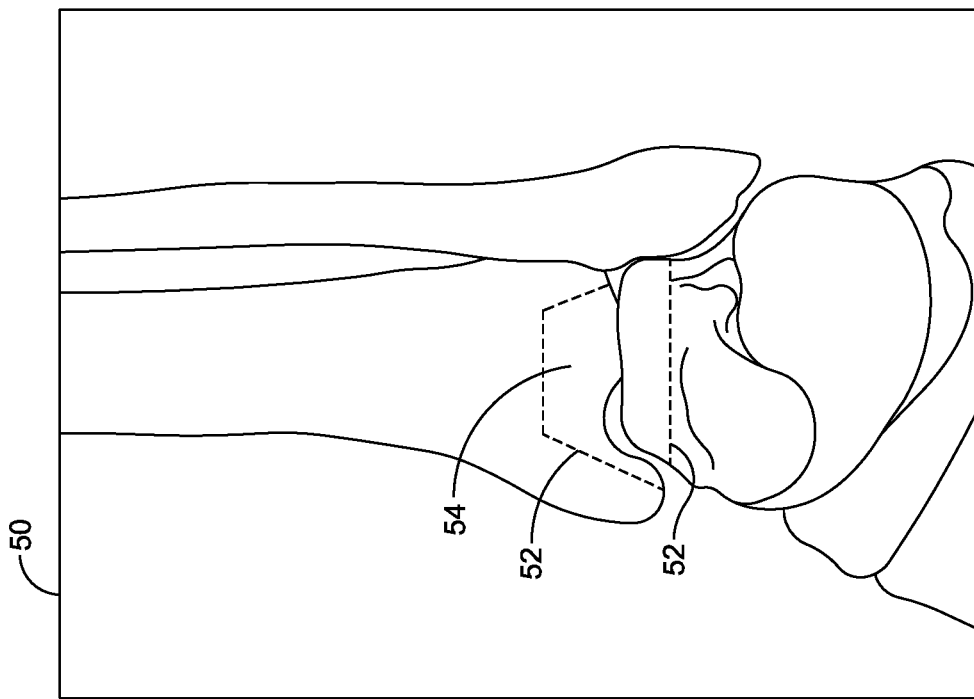

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top," "bottom," "proximal," "distal," "superior," "inferior," "medial," and "lateral" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected," refer to a relationship wherein structures are secured or attached to one another either directly or indirectly through intervening structures, as well as both movable or rigid attachments or relationships, unless expressly described otherwise. Like elements have been given like numerical designations to facilitate an understanding of the present subject matter.

As used herein, the term "substantially" denotes elements having a recited relationship (e.g., parallel, perpendicular, aligned, etc.) within acceptable manufacturing tolerances. For example, as used herein, the term "substantially parallel" is used to denote elements that are parallel or that vary from a parallel arrangement within an acceptable margin of error, such as +/−5°, although it will be recognized that greater and/or lesser deviations can exist based on manufacturing processes and/or other manufacturing requirements.

The disclosed systems and methods may advantageously utilize custom manufactured surgical instruments, guides, and/or fixtures that are based upon a patient's anatomy to maximize the accuracy of the guides and/or surgical instruments during a surgical procedure. These custom instruments, guides, and/or fixtures may be created by imaging a patient's anatomy with a computer tomography ("CT") scanner, a magnetic resonance imaging ("MRI") machine, or like medical imaging technology prior to surgery and utilizing these images to create patient-specific instruments, guides, and/or fixtures. This is generally termed as a preoperative assessment or plan and may be used in conjunction with intra-operative tools to accurately implement such a plan. Exemplary preoperative assessments or plans may allow a surgeon to specify the size, position, and/or orientation of a patient's anatomical components and/or subsequent implant components within the joint or bone at issue based upon preoperative CT or MRI images. Of course, final component size and position may be determined intra-operatively through direct visualization of the implants or various sizing instrumentation by the surgeon with or without the aid of fluoroscopy.

The disclosed systems and methods can be applied to a revision surgery for primary replacement of ankle joint 12. Examples of primary ankle techniques using patient-specific surgical jigs and fixtures are described in U.S. Patent Appl. Pub. No. 2015/0257899, published Sep. 17, 2015, entitled "Ankle Replacement System and Method" and U.S. Pat. No. 8,808,303, issued on Aug. 19, 2014 and entitled "Orthopedic Surgical Guide," each of which is incorporated by reference herein in its entirety. Although the following description of the custom patient-specific instruments are described with respect to a foot 10 and ankle 12 (FIG. 1), one of ordinary skill in the art will understand that the systems and methods may be utilized in connection with other joints including, but not limited to, knees, hips, shoulders, and the like. As shown in FIG. 1, a typical human foot 10 includes an ankle joint 12 formed between a talus 14, which is disposed on a calcaneus 20, a tibia 16, a fibula 18, and a navicular 22.

Upon completion of a primary replacement surgery, one or more articulation surfaces of ankle joint 12 are replaced with one or more implants. For example, in some embodiments, tibial implant and/or a talar implant replace articulation surfaces of a talus 12 and/or a tibia 14, respectively. A revision procedure is applied to a joint that has previously been subject to a replacement procedure. The revision procedure modifies the joint replacement through making additional resections, replacing existing implants with alternative implants, and/or adding additional or removing implants at the joint. For example, in some embodiments, the systems and methods disclosed herein can be used for an ankle revision procedure in which the ankle joint has previously been subject to a replacement procedure.

During a primary and/or a revision surgery, a CT or MRI scanned image or series of images may be taken of a patient's ankle 12 (or other joint) and then converted from, e.g., a DICOM image format, to a solid computer model of the ankle including the calcaneus, talus, tibia, navicular, and fibula to determine implant alignment, type, and sizing using specialized modeling methods that are often embodied in computer software. Computer generated models (e.g., CAD models) that are derived from the data of the CT or MRI scan image will often include precise and accurate information regarding the surface contours surrounding the structures that have been imaged, e.g., the surface topography of the bones or contour of connected tissue (e.g., fascia, cartilage, etc.) that have been imaged. Imaging and generation of patient-specific implants is further described in U.S. Pat. No. 5,768,134, issued on Jun. 16, 1998, entitled "Method for Making a Perfected Medical Model on the Basis of Digital Image Information of a Part of the Body," which is incorporated herein by reference in its entirety. In some embodiments, the CT and/or MRI scan image includes foreign bodies, such as one or more implants previously installed in the joint 12 during a primary replacement surgery, as described in greater detail in International Patent Application No. PCT/US15/20414, which published as WO 2016/148675, which is incorporated herein in its entirety. It will be understood that by surface topography it is meant the location, shape, size and distribution of surface features such as concavities and prominences or the like.

In some embodiments, after establishing a primary ankle replacement, a revision procedure can be performed re-using instrumentation from the primary replacement procedure and/or using additional instrumentation. For example, in some embodiments, a revision procedure can include the use of a conversion instrument 200. The conversion instrument 200 is configured to couple a cutting guide to one of the first bone 14 and/or the second bone 16 to allow one or more revision resections to be formed. The revision resections are configured to further modify the first bone 14 and/or the second bone 16 to receive alternative and/or additional revision implants.

Figure 3:
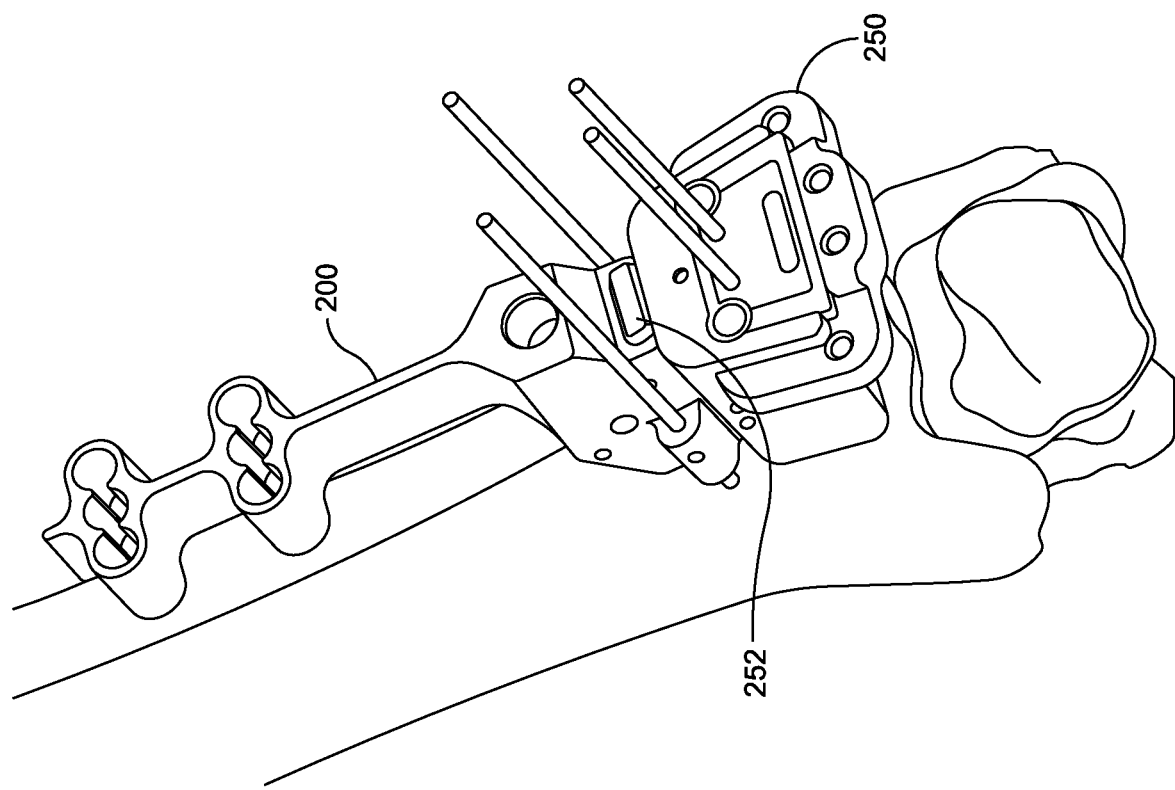
FIG. 3 illustrates a bone preparation instrument coupled to a first bone by a conversion instrument, in accordance with some embodiments.
Figure 5:
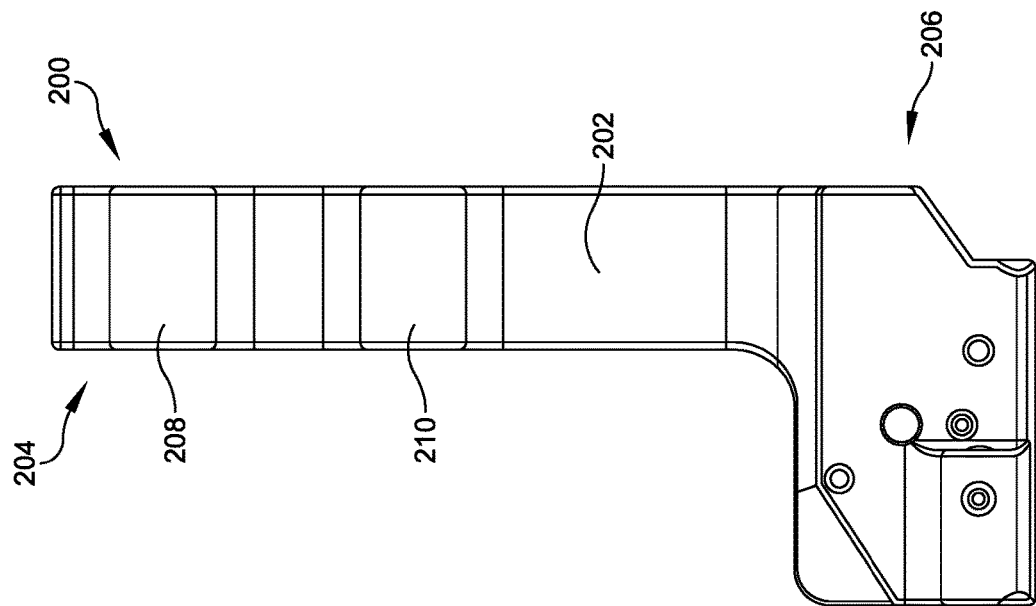
FIG. 5 illustrates a side view of the bone preparation instrument of FIG. 3, in accordance with some embodiments.
Figure 4:
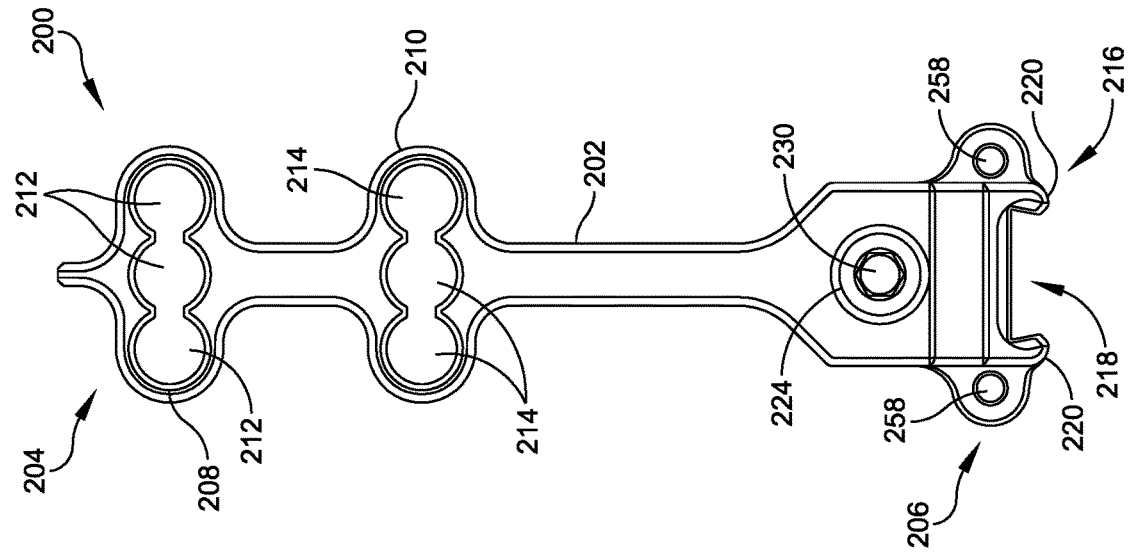
FIG. 4 illustrates a front side plan view of the bone preparation instrument of FIG. 3, in accordance with some embodiments.

As illustrated in FIGS. 3-5, in some embodiments, a guide 250 and a conversion instrument 200 can be coupled to a first bone 14 by sliding the guide 250 and/or the conversion instrument 200 over one or more pins inserted into the first bone 14. As best seen in FIG. 4, conversion instrument 200 includes an elongate body 202 extending from a region for fixation (shown at the proximal end 204 in the illustrated embodiment) to a region for attaching other bone preparation instruments (shown at the distal end 206 in the illustrated embodiment). Conversion instrument 200 includes a first and second oblong sections 208, 210 that extend transversely with respect to the longitudinal direction of instrument 200. Each oblong section 208, 210 defines a respective plurality of interconnected holes 212, 214.

The distal end 206 of instrument 200 includes a dovetail joint 216 defining a cavity 218 between rails 220 at the distal end 206 of instrument 200. Cavity 218 is sized and configured to receive a locking wedge 222 as best seen in FIG. 5. A through-hole 224 extends from a first side 226 to a second side 228 of the distal end 206 of instrument 200 and is sized and configured to receive a locking bolt 230 therein. Locking bolt 230 is configured to a press locking wedge against a dovetail member 252 of a guide 250, such as a cut guide, a drill guide, and/or coronal sizing and drill guide. Holes 258 are defined by the distal end 206 of instrument 200 on either side of dovetail joint 216. Holes 258 are sized and configured to receive pins 210 therein.

The conversion instrument 200 can be secured to a guide 250 by having dovetail extension 252 of guide 250 be received within dovetail joint 216. A hex driver is used to tighten locking bolt 230 within hole 224. The rotation of locking bolt 230 causes the engagement end of locking bolt, which can be threaded or have another engagement feature disposed thereon, engage a corresponding structure disposed within distal end of instrument 200 and axially move such that shoulders of bolt 230 contact angled surfaces of a locking wedge. The axial movement of bolt 230 forces the bottom surface of the locking wedge against dovetail extension, which is frictionally locked by rails 220. Additional examples of positioning and use of the conversion instrument 200 are disclosed in U.S. Pat. Appl. Pub. 2015/0257899, published on Sep. 17, 2015, and entitled "Ankle Replacement System and Method," which was previously incorporated herein in its entirety.

As discussed above, during a revision surgery, one or more additional and/or alternative revision cuts can be formed in a bone, such as first bone 14 and/or second bone 16. In some embodiments, a revision cutting guide can be positioned with reference to a preoperatively planned deformity correction based on anatomic references and/or surgeon preferences. The joint 12 can be positioned to match the pre-operatively planned deformity correction using a spacer assembly. The spacer assembly positions the first bone 14 and/or the second bone 16 in the preoperatively planned deformity correction and further guides the placement of a revision cutting guide, as discussed in greater detail below.

FIG. 6 illustrates a spacer assembly 300 positioned between a first bone 14 and a second bone 16 of a joint 12 and an adjustable guide 600 coupled thereto, in accordance with some embodiments. Spacer assembly 300 includes a first spacer 400 and a second spacer 500. First spacer 400 and second spacer 500 are configured to position the first bone 14 and the second bone 16 in a corrected alignment. In some embodiments, the corrected alignment of joint 12 corresponds to a preoperatively planned deformity correction that is planned based on anatomic references and/or surgeon preferences. Spacers 400, 500 set one or more degrees of freedom of joint 12. For example, in various embodiments, the spacers 400, 500 can correct one or more of a varus/valgus orientation, a flexion/extension orientation, an inversion/eversion orientation, an anterior/posterior position, a medial/lateral position, and/or a proximal/distal position between the first bone 14 and the second bone 16 intraoperatively. The first spacer 400, the second spacer 500, and/or the adjustable guide 600 may be manufactured from a resilient polymer material of the type that is suitable for use in connection with stereo lithography, selected laser sintering, 3D printing, or the like manufacturing equipment, e.g., a polyamide powder repaid prototype material is suitable for use in connection with the selective laser sintering.

Figure 9:
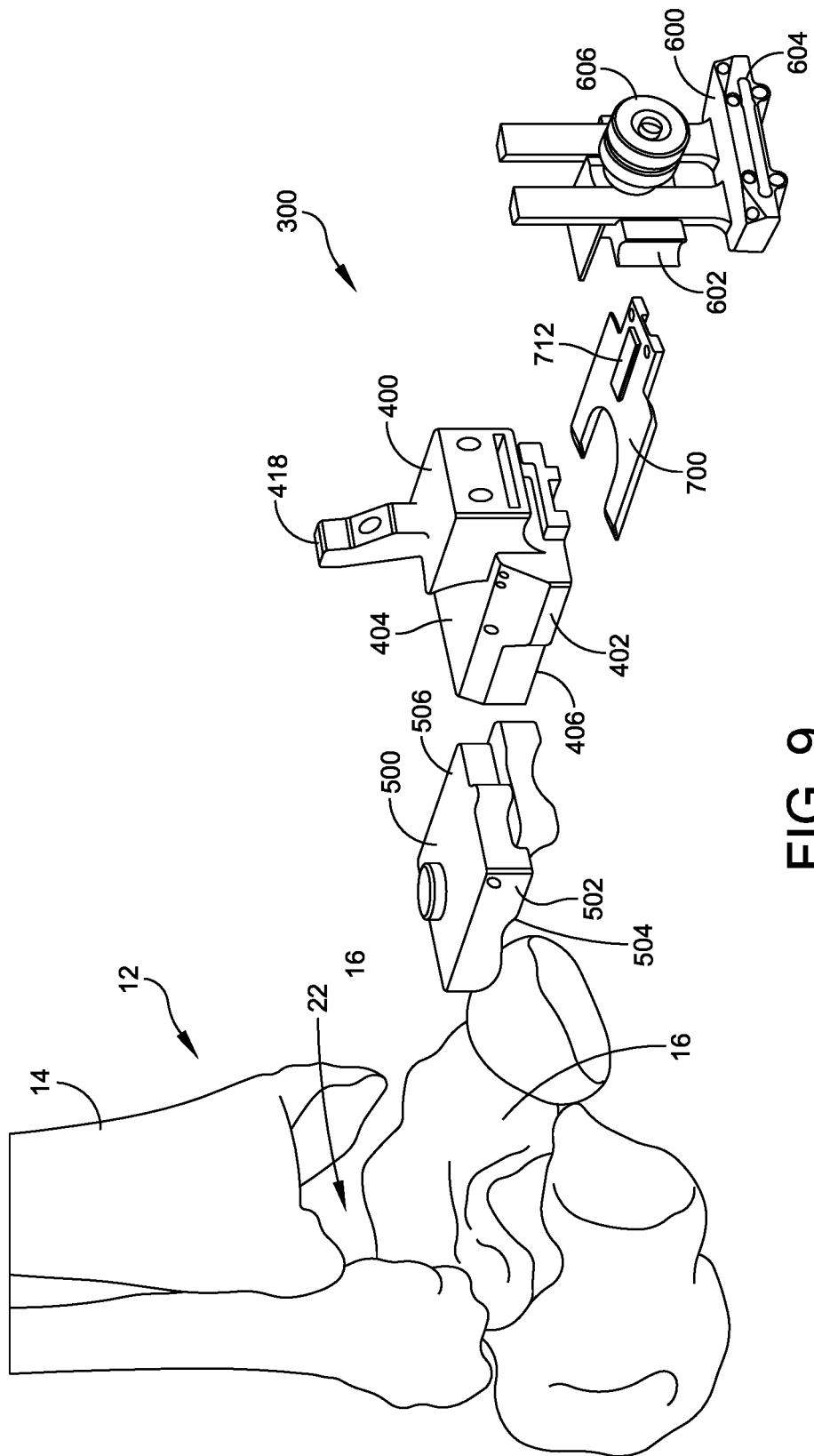
FIG. 9 illustrates an exploded view of the spacer assembly of FIG. 6, in accordance with some embodiments.

As illustrated in FIG. 9, first spacer 400 includes a first (or bone contacting) surface 404 configured to abut first bone 16 and second spacer 500 includes a first (or bone contacting) surface 504 configured to abut second bone 16. Each of first spacer 400 and second spacer 500 further include respective second (or coupling) surfaces 406, 506 configured to be positioned in an abutting relationship. When spacers 400, 500 are positioned against respective first and second bones 14, 16, respective coupling surfaces 406, 506 are abutting and position first and second bones 14, 16 to surface-match the anatomy of the joint 12 in a corrected alignment. For example, in various embodiments, the spacers 400, 500 position the first bone and a second bone in one or more of a pre-operatively determined varus/valgus orientation, flexion/extension orientation, inversion/eversion orientation, anterior/posterior position, medial/lateral position, and/or proximal/distal position. Although embodiments are discussed having a first spacer 400 and/or a second spacer 500 coupled to a bone, it will be appreciated that the first spacer 400 and/or the second spacer 500 can be coupled to an implant installed in a bone, such as an implant installed during a prior replacement surgery and/or installed concurrently during a current replacement and/or revision surgery.

Figure 7:
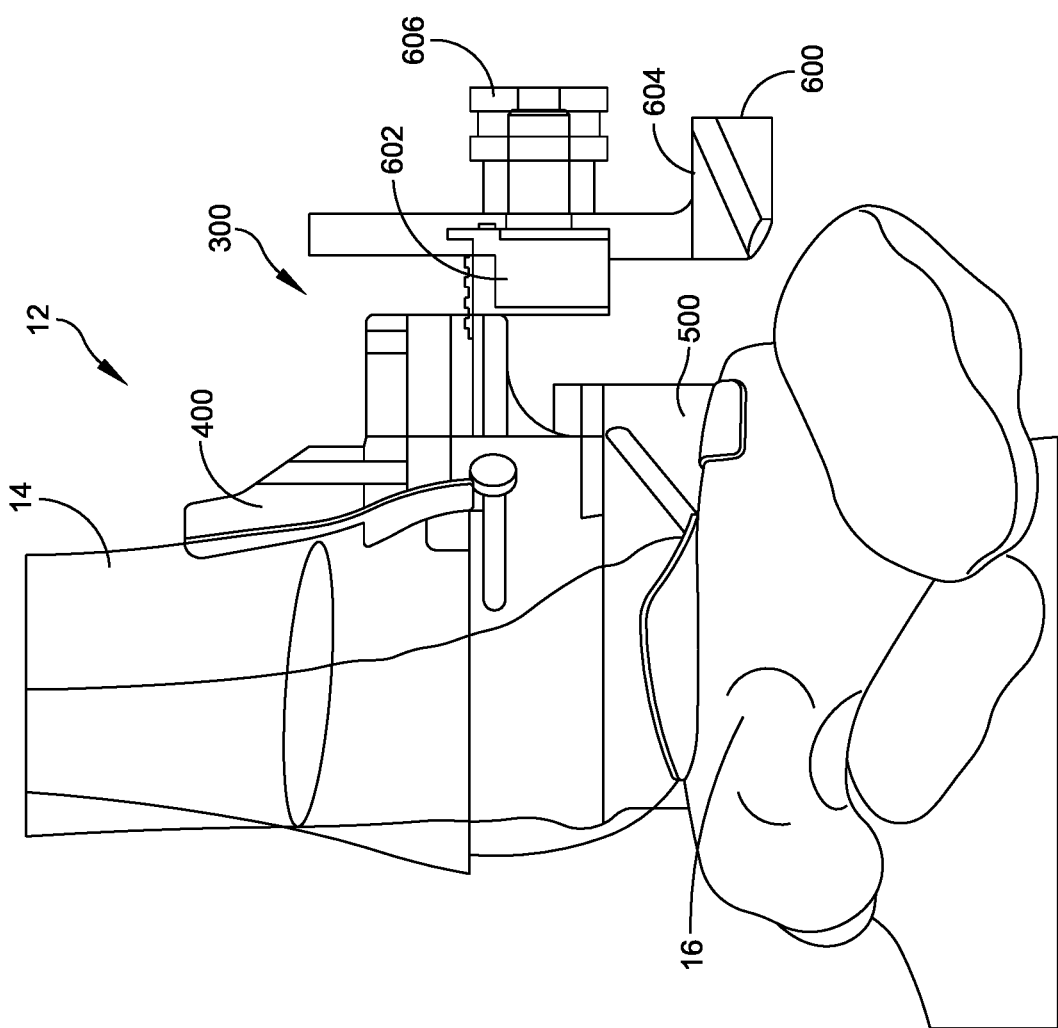
FIG. 7 illustrates a side view of the spacer assembly of FIG. 6, in accordance with some embodiments.
Figure 8:
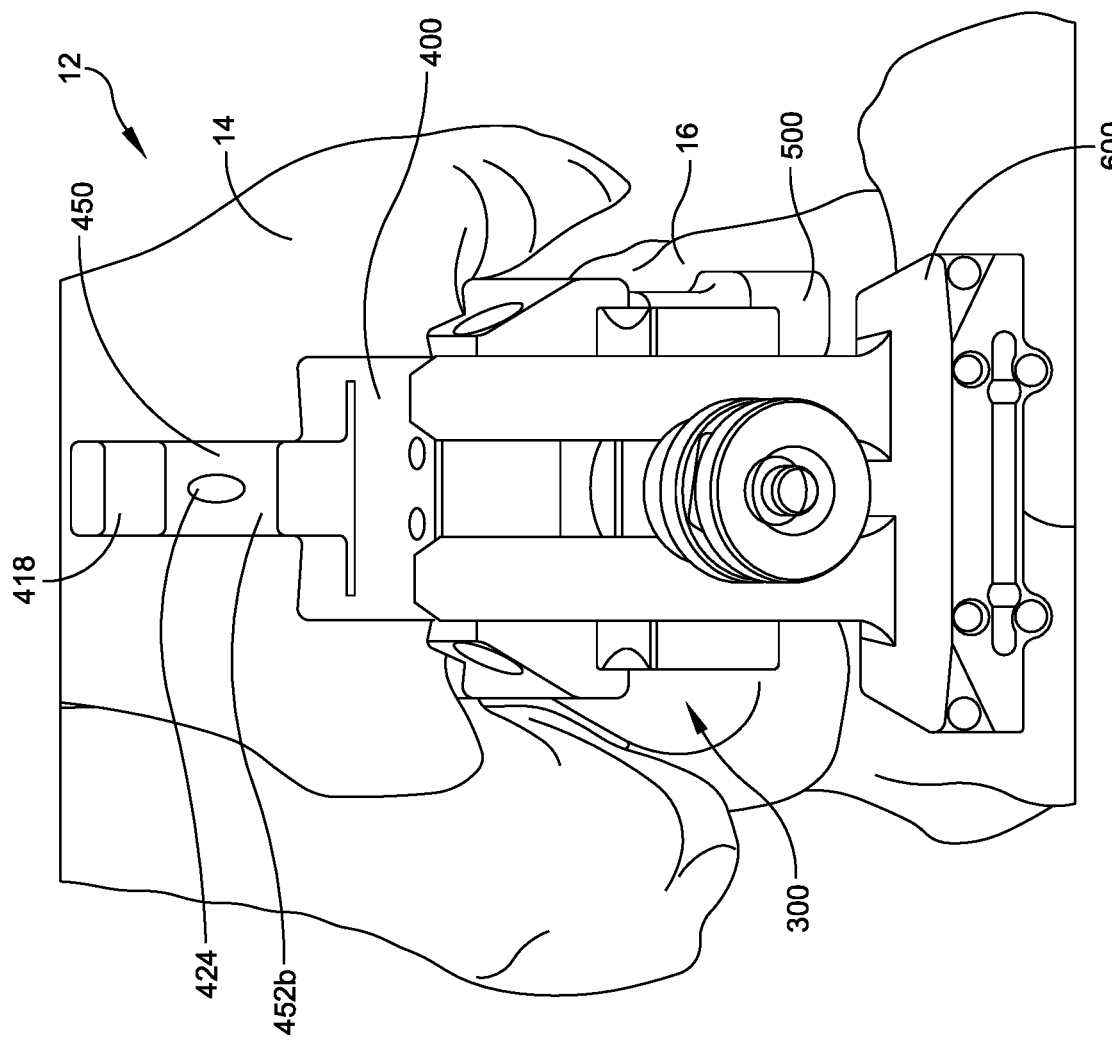
FIG. 8 illustrates a front view of the spacer assembly of FIG. 6, in accordance with some embodiments.

As best shown in FIG. 7, in some embodiments, an adjustable guide 600 is configured to couple to one or both of first spacer 400 and/or second spacer 500. Adjustable guide 600 is adjustable in one or more directions with respect to spacers 400, 500 and/or the joint 12 to set a resection depth and/or position for first bone 14 and/or second bone 16. For example, in some embodiments, adjustable guide 600 is adjustable in a proximal/distal direction, a superior/inferior direction, and/or any other suitable direction with respect to spacers 400, 500. The adjustable guide is configured to locate a revision cut in second bone 16. Although embodiments are discussed herein including an adjustable guide 600 configured to locate a revision cut in second bone 16, it will be appreciated that adjustable guide 600 can include guide elements corresponding to additional and/or alternative cuts and/or revisions in first bone 14 and/or second bone 16.

Figure 10:
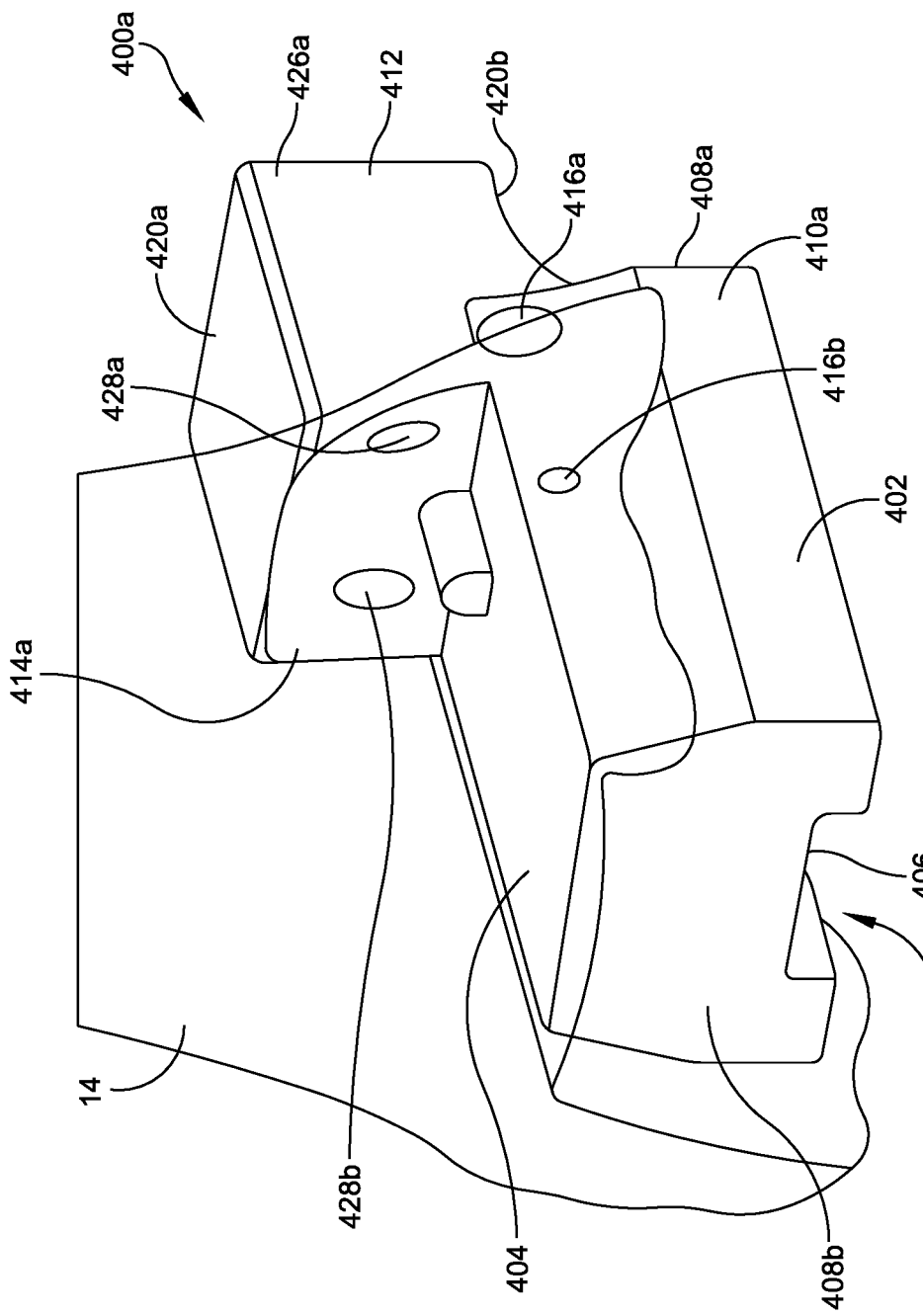
FIG. 10 illustrates an isometric view of a first spacer positioned within a resected bone space of a first bone, in accordance with some embodiments.
Figure 11:
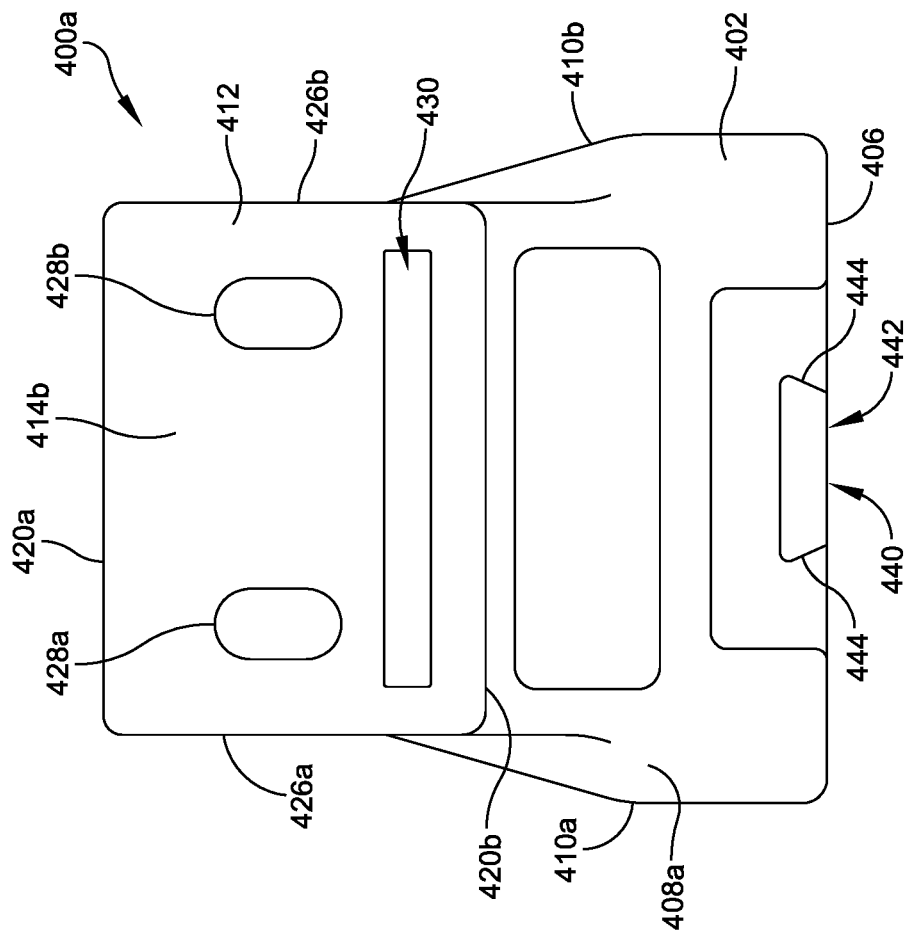
FIG. 11 illustrates a front view of the first spacer of FIG. 10, in accordance with some embodiments.
Figure 12:
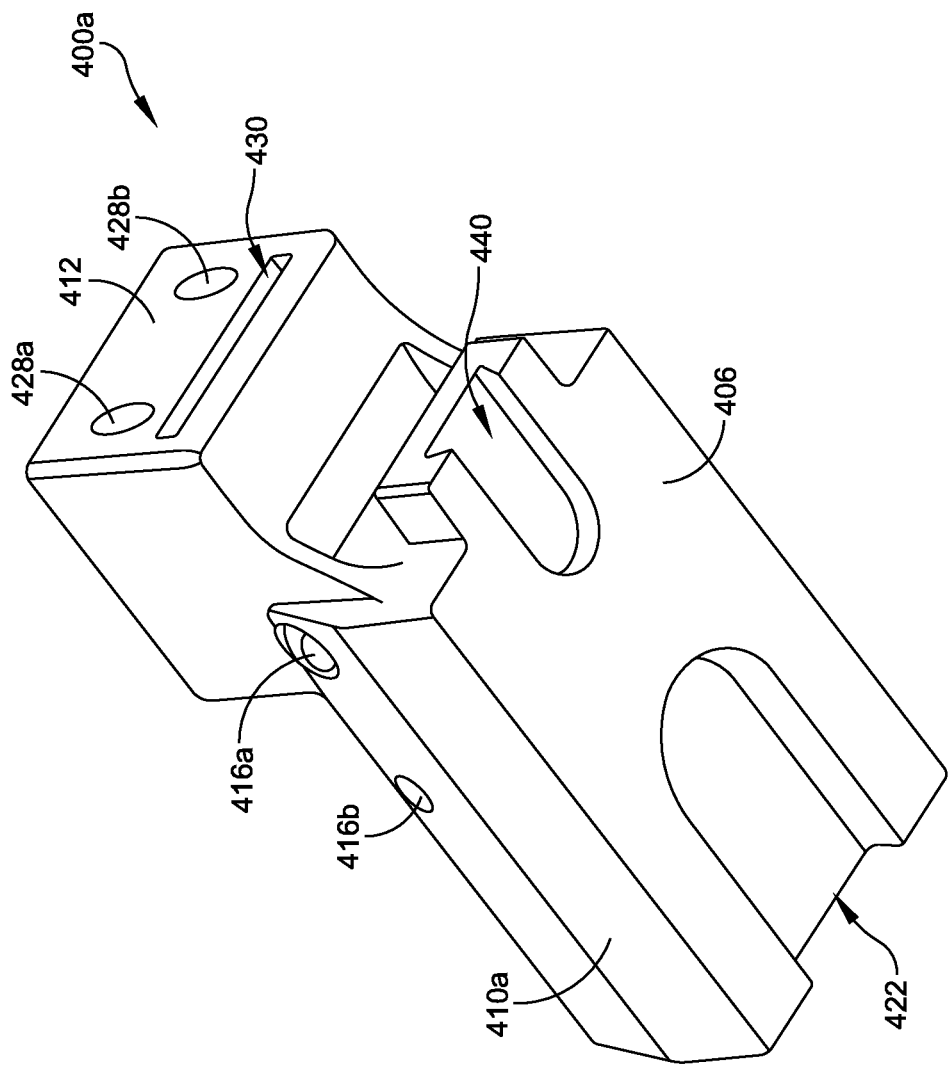
FIG. 12 illustrates a bottom isometric view of the first spacer of FIG. 10, in accordance with some embodiments.

FIGS. 10-12 illustrate a first spacer 400a configured to abut first bone 14, in accordance with some embodiments. In some embodiments, first spacer 400a is configured to interface with existing bone, cartilage, and/or other soft tissue of first bone 14. For example, in some embodiments, first spacer 400a is a tibial spacer configured to abut a tibia. In other embodiments, first spacer 400a is configured to abut a pre-existing implant coupled to the first bone 14. The pre-existing implant can include an implant inserted during a previous ankle replacement surgery and/or inserted during a current ankle replacement surgery.

Spacer 400a includes a body 402 having a thickness extending between a bone contacting surface 404 and an opposing coupling surface 406. Body 402 further extends longitudinally between a proximal surface 408a and a distal surface 408b, as best seen in FIG. 10, and has a width extending between a first side surface 410a and a second side surface 410b as best seen in FIG. 11. Body 402 is sized and configured for insertion into a resected portion of first bone 14. Bone contacting surface 404 defines a patient-specific profile complimentary to a surface of the first bone 14. For example, bone contacting surface 404 can be configured to interface with existing bony anatomy of first bone 14 and/or cartilage or other soft tissue coupled to first bone 14.

As best seen in FIGS. 10 and 12, body 402 defines one or more first fixation holes 416a, 416b extending therethrough. First fixation holes 416a, 416b extend from one of first or second side surfaces 410a, 410b to the other of first and second side surfaces 410a, 410b. The fixation holes 416a, 416b are angled with respect to first and second side surfaces 410a, 410b such a first side of each of the fixation holes 416a, 416b is positioned proximally of a second side. In some embodiments, fixation holes 416a, 416b extend through body 402 along intersecting hole axis, although it will be appreciated that the fixation holes 416a, 416b can extend through the body 402 along non-intersecting hole axis in some embodiments.

In some embodiments, a bone engaging structure 412 extends from a proximal surface 408a of body 402 in a superior direction above bone contacting surface 404. Bone engaging structure 412 has a length extending between a bone contacting surface 414a and an opposing surface 414b, a thickness extending between an upper surface 420a and a lower surface 420b, and a width extending between a first side surface 426a and a second side surface 426b. In some embodiments, bone contacting surface 414a includes a patient-specific profile configured to surface-match a portion of first bone 14 and/or soft-tissue coupled to first bone 14. Bone engaging structure 412 is configured to abut a surface of first bone 14 and maintain the first spacer 400a in a fixed anterior/posterior position with respect to first bone 14. In some embodiments, the portion of the first bone 14 that is surface-matched by bone engaging structure 412 is the anterior surface of a tibia, although one of ordinary skill in the art will understand that bone engaging structure can be configured to surface match other bones and surfaces.

Referring now to FIG. 11, bone engaging structure 412 defines a slot 430 extending from opposing surface 414b at least partially into block 412. In some embodiments, slot 430 extends from opposing surface 414b to bone contacting surface 414a. Slot 430 is sized and configured to receive a portion of a resection guide 600 therein, such as a flat coupling element 612 described in greater detail with respect to FIGS. 18-21. In some embodiments, bone engaging structure 412 defines one or more second fixation holes 428a-428b extending from opposing surface 414b to bone contacting surface 414a. Second fixation holes 428a-428b are each sized and configured to receive a fixation element therethrough. The fixation elements can include any suitable fixation element, such as a k-wire, screw, pin, and/or any other suitable fixation element. In some embodiments, the fixation elements are configured to maintain first spacer 400 in a fixed position with respect to first bone 14. In some embodiments, first fixation holes 416a-416b and/or second fixation holes 428a-428b include a position corresponding to one or more fixation elements previously coupled to the first bone 14 by one or more additional surgical elements.

In some embodiments, coupling surface 406 of spacer 400a is configured to abut and/or couple to spacer 500 as best seen in FIG. 6. Coupling surface 406 includes a recess 422 extending from a proximal edge of coupling surface 406 proximally into the body 402. Recess 422 is sized and configured to receive a complementary coupling feature of second spacer 500, such as a mating protrusion 510, discussed in greater detail with respect to FIGS. 14-15. Recess 422 couples first spacer 400a to second spacer 500 in a predetermined arrangement. In some embodiments, recess 422 is a U-shaped recess, although it will be appreciated that recess 422 can have any shape complementary to the shape of mating protrusion 510 of second spacer 500.

In some embodiments, coupling surface 406 defines a dovetail joint 440. Dovetail joint 440 has a similar construction to the dovetail joint 216 described above with respect to the conversion instrument 200. A cavity 442 is defined in a coupling surface 406 between rails 444 as best seen in FIG. 11. Cavity 442 is sized and configured to receive a corresponding dovetail extension 712 extending from a shim 700, as discussed in greater detail with respect to FIGS. 16-17. Although embodiments are discussed herein including a dovetail joint 440, it will be appreciated that the coupling surface 406 can define any suitable structure or cavity sized and configured to couple to an extension 712 defined by the shim 700. In some embodiments, the dovetail joint 440 is omitted.

Figure 13:
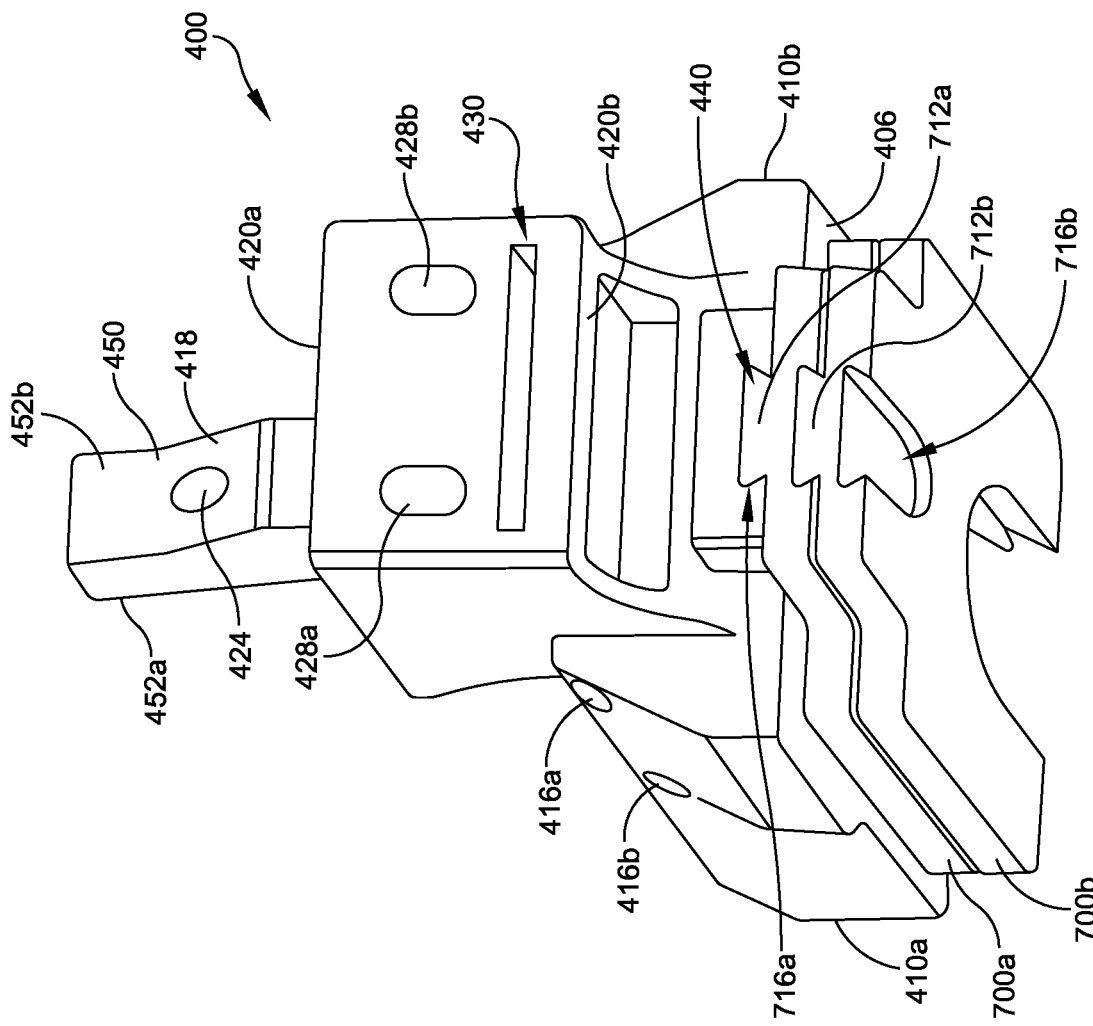
FIG. 13 illustrates another embodiment of a first spacer configured to be positioned within a resected bone space of a first bone, in accordance with some embodiments.

With reference to FIG. 13, in some embodiments, a first spacer 400 includes a bone engaging extension 418 extending from an upper surface 420a of bone engaging structure 412. Bone engaging extension 418 extends above upper surface 420a of the bone engaging structure 412. Bone engaging extension 418 includes a body 450 extending between a bone contacting surface 452a and an opposing surface 452b. In some embodiments, bone contacting surface 452b is surface-matched to a portion of first bone 14. Bone engaging extension 418 defines at least alignment hole 424 extending therethrough. Alignment hole 424 is configured to provide a visual indication during fluoroscopy and/or other imaging procedures to ensure proper alignment of the first spacer 400 prior to insertion of one or more fixation elements.

Figure 14:
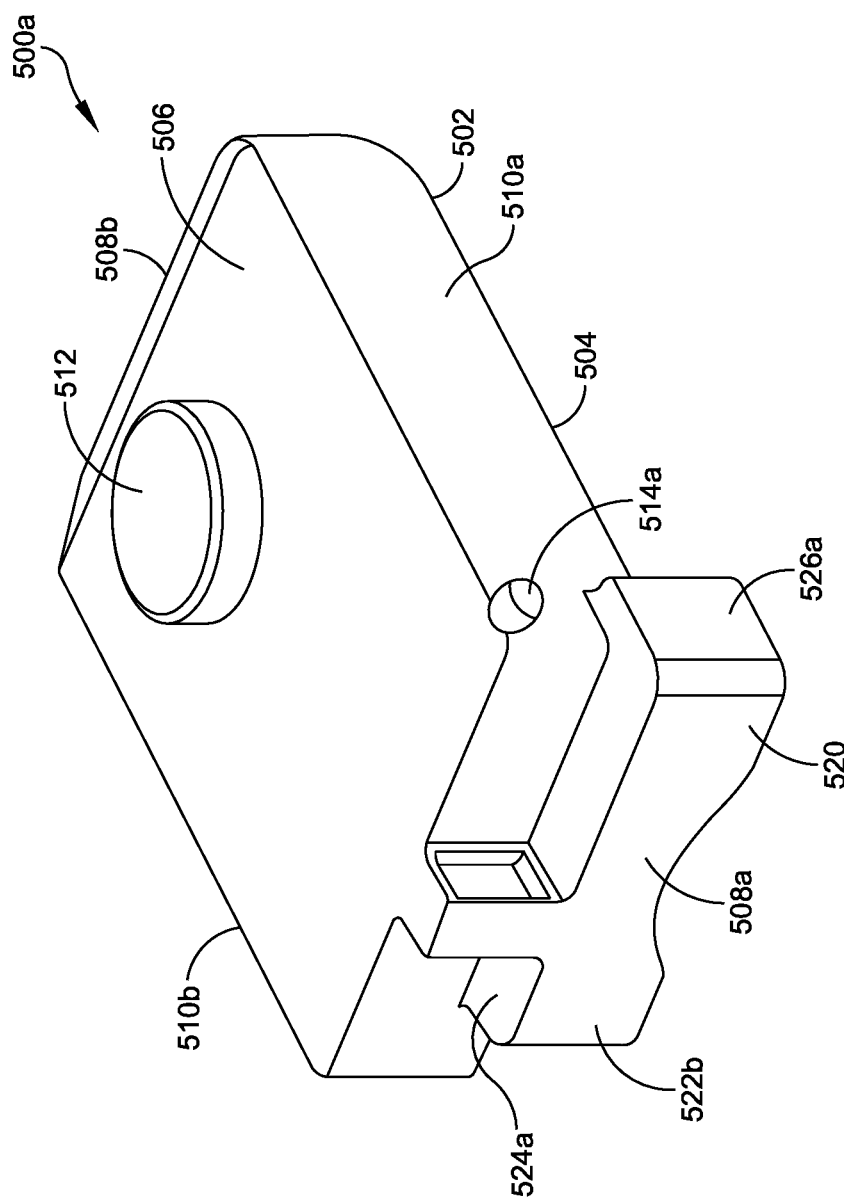
FIG. 14 illustrates an isometric view of a second spacer configured to abut a second bone, in accordance with some embodiments.
Figure 15:
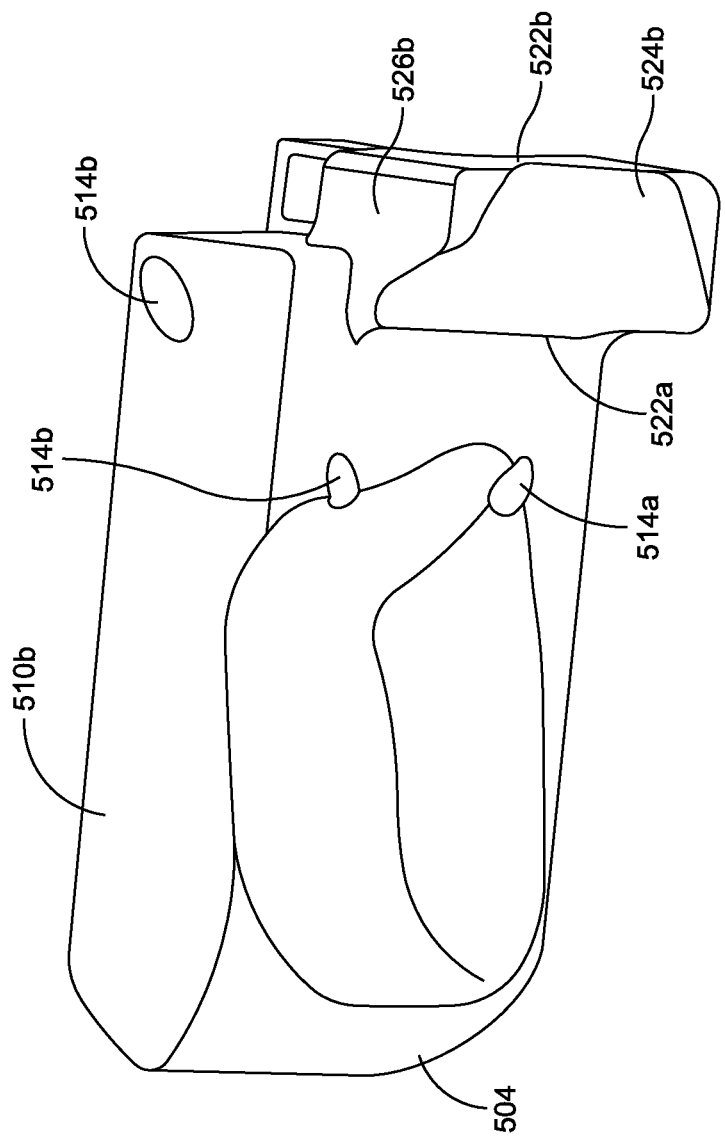
FIG. 15 illustrates a bottom isometric view of the second spacer of FIG. 14, in accordance with some embodiments.
Figure 18:
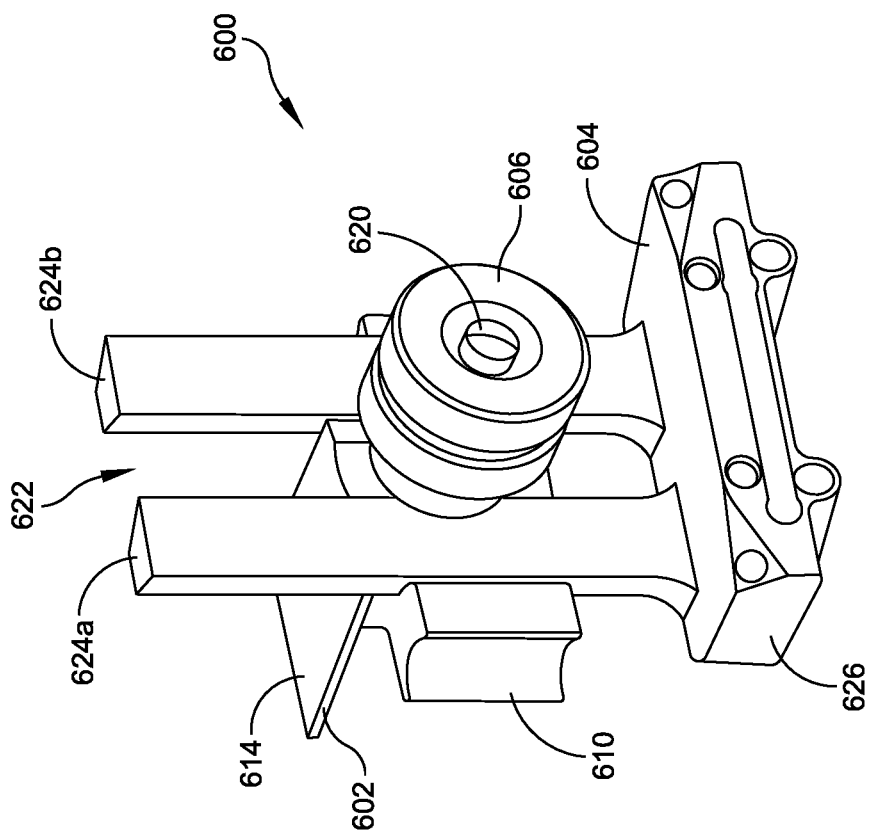
FIG. 18 illustrates an isometric view of an adjustable guide, in accordance with some embodiments.
Figure 19:
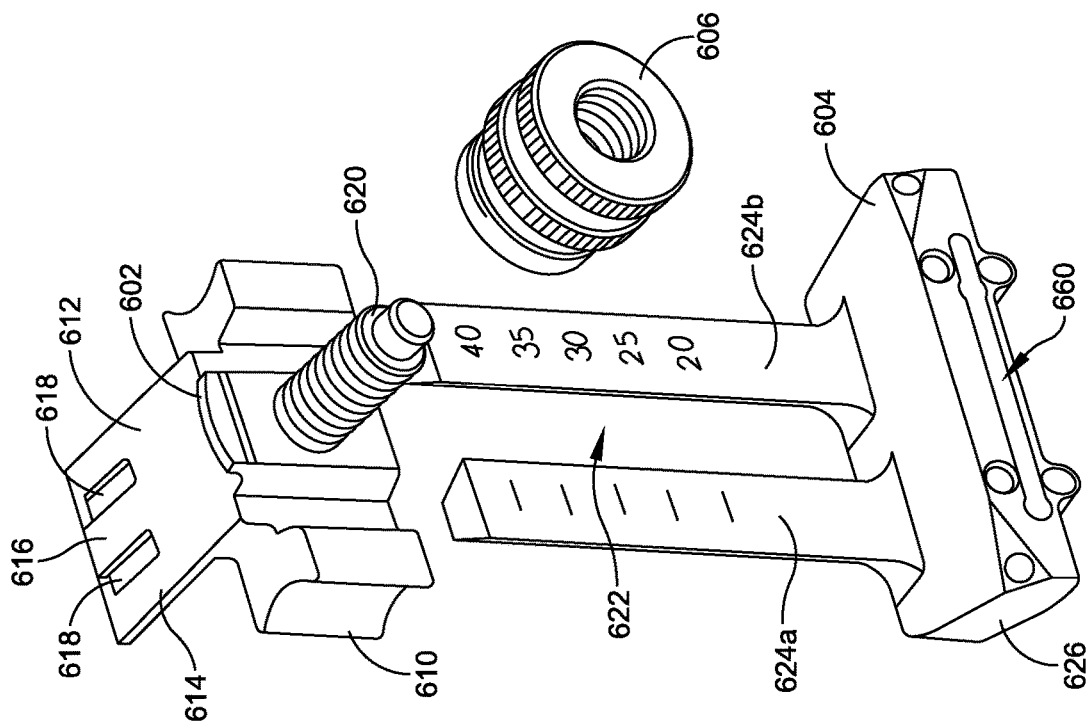
FIG. 19 illustrates an exploded view of the adjustable guide of FIG. 18, in accordance with some embodiments.

FIGS. 14-15 illustrates another example of a second spacer 500a configured to abut second bone 16, in accordance with some embodiments. The second spacer 500a is similar to the second spacer 500 discussed above in conjunction with FIGS. 6-9, and similar description is not repeated herein. Second spacer 500a is configured to interface with existing bone, cartilage, and/or other soft tissue of second bone 16. For example, in some embodiments, second spacer 500a is a talar spacer configured to abut a talus. In other embodiments, second spacer 500a is configured to abut a pre-existing implant coupled to second bone 16. The pre-existing implant can include an implant inserted during a previous ankle replacement surgery and/or inserted during a current ankle replacement surgery.

In some embodiments, second spacer 500a includes a body 502 having a thickness extending between a bone contacting surface 504 and a coupling surface 506. The body 502 further extends longitudinally between a proximal surface 508a and a distal surface 508b and has a width extending between a first side surface 510a and a second side surface 510b. Body 502 is sized and configured to abut a portion of second bone 16 and/or soft tissue coupled to second bone 16, such as a resected and/or non-resected superior surface of second bone 16. In some embodiments, bone contacting surface 504 defines a patient-specific profile surface-matched to second bone 14.

Coupling surface 506 is positioned in an opposing relationship with coupling surface 406 of first spacer 400a when first and second spacers 400a, 500a are positioned within joint 12. In some embodiments, each of the coupling surfaces 406, 506 define a planar surface. Coupling surface 506 can have a greater, lesser, and/or equal surface area as coupling surface 406. Although embodiments are discussed herein including planar coupling surfaces 406, 506, it will be appreciated that coupling surfaces 406, 506 can have any suitable matching surface topography configured to position first bone 14 and second bone 16 in one or more of a pre-operatively determined varus/valgus orientation, flexion/extension orientation, inversion/eversion orientation, anterior/posterior position, medial/lateral position, and/or proximal/distal position.

In some embodiments, a mating element 512 extends from coupling surface 506. Mating element 512 is sized and configured to couple second spacer 500a to one or more superiorly positioned elements, such as first spacer 400a. In some embodiments, mating element 512 includes a cylindrical protrusion sized and configured to be received within channel 420 formed in coupling surface 406. The coupling between mating element 512 and channel 420 provides constraint of one or more degrees of freedom (such as medial/lateral, proximal/distal etc.) of joint 12 while allowing for adjustment of one or more other degrees of freedom (such as internal/external rotational flexibility, anterior/posterior translation, etc.) of joint 12. Although embodiments are discussed herein including a cylindrical protrusion, it will be appreciated that mating element 512 can include any suitable cross-section configured for insertion into channel 420 and can extend any suitable distance above coupling surface 506.

In some embodiments, second spacer 500a defines one or more fixation holes 514a-514b each being respectively sized and configured to receive a fixation element therein. Fixation holes 514a-514b extend from a first surface, such as coupling surface 506 and/or proximal surface 508a, to a second surface, such as bone contact surface 504 and/or distal surface 508b. Each of the fixation elements can include any suitable fixation element, such as a k-wire, a screw, and a pin, to list only a few possibilities. Second spacer 500a is maintained in a fixed position with respect to second bone 16 by inserting one or more fixation elements through one or more of fixation holes 514a-514b. In some embodiments, one or more of fixation holes 514a-514b include a position corresponding to a fixation element previously coupled to second bone 16 by one or more additional surgical instruments and/or guides.

In some embodiments, a bone engaging structure 520 extends in an inferior direction from the body 502. The bone engaging structure has a length extending between a bone contacting surface 522a and an opposing surface 522b, a thickness extending between an upper surface 524a and a lower surface 524b, and a width extending between a first side surface 526a and a second side surface 526b. In some embodiments, bone contacting surface 522a and/or lower surface 524b include a patient-specific profile configured to surface-match a portion of first bone 16 and/or soft-tissue coupled to first bone 16. Bone engaging structure 520 is configured to abut a surface of first bone 16 and maintain second spacer 500a in a fixed anterior/posterior position with respect to second bone 16.

In some embodiments, laxity can exist between first bone 14 and second bone 16 after installation of the first spacer 400 and/or the second spacer 500. Laxity in joint 12 may not be fully known pre-operatively and/or may change intra-operatively, for example, due to ligament release, tendon release, tendon transfer, osteotomy, etc. In some embodiments, one or more shims 700 can be inserted between respective spacers 400, 500 to distract first bone 14 from second bone 16. FIGS. 16-17 illustrate a shim 700 configured to be positioned between first spacer 400 and second spacer 500 to correct laxity in joint 12, in accordance with some embodiments. Shim 700 may be manufactured from a resilient polymer material of the type that is suitable for use in connection with stereo lithography, selected laser sintering, or the like manufacturing equipment, e.g., a polyamide powder repaid prototype material is suitable for use in connection with the selective laser sintering.

Shim 700 includes a body 702 extending between an upper surface 704 and a lower surface 706. Body 702 has a predetermined thickness extending from the upper surface 704 to the lower surface 706, such as, for example, a thickness in the range of 1 mm-6 mm, such as 1 mm, 2 mm, 2.5 mm, 3 mm, 3.5 mm, 4 mm, 5 mm, and/or any other suitable thickness. Body 702 extends longitudinally between a proximal side 708a and a distal side 708b and has a width extending between a first side 710a and a second side 110b. In some embodiments, body 702 can have a generally rectangular shape, although it will be appreciated that body 702 can have any suitable regular and/or irregular shape configured to be received within a joint space between a first bone and a second bone. In some embodiments, body 702 is sized and configured to correspond to one or more of the coupling surfaces 406, 506 of respective first and second spacers 400, 500.

In some embodiments, upper surface 704 includes a dovetail extension 712 configured to couple shim 700 to first spacer 400 and/or a shim positioned in contact with the upper surface 704. The dovetail extension 712 includes a projection 714 sized and configured to be inserted within cavity 442 formed in first spacer 400. The dovetail extension 712 is positioned at a proximal edge of the upper surface 704, although it will be appreciated that dovetail extension 712 can extend from any suitable location of upper surface 704 such that dovetail extension 712 is aligned with cavity 442 when shim 700 is aligned with first spacer 400. In some embodiments, the dovetail extension 712 is omitted. Although embodiments are discussed herein including a dovetail extension 712, it will be appreciated that the shim 700 can be coupled to the first spacer using any suitable coupling elements, such as a non-dovetail projection, a fixation device, a magnetic coupling, one or more rails, a ball-detent coupling, a spring-clip coupling, and/or any other suitable connection.

In some embodiments, a recess 716 is defined in lower surface 706 of shim 700. Recess 716 is sized and configured to receive protrusion 510 of second spacer 500. Recess 716 couples shim 700 to second spacer 500. In some embodiments, protrusion 510 and recess 716 constrain one or more degrees of freedom of joint 12 (such as medial/lateral position, proximal/distal position, flexion/extension orientation, etc.) while allowing adjustment of one or more other degrees of freedom (such as inversion/eversion orientation, anterior/posterior position, etc.). In some embodiments, recess 716 is similar and/or identical to recess 422 formed in first spacer 400. Although embodiments are illustrated having a shim 700 positioned between first spacer 400 and second spacer 500, it will be appreciated that one or more shims 700 can be positioned between first spacer 400 and first bone 14 and/or second spacer 500 and second bone 16, and are within in the scope of this disclosure. In some embodiments, the bone contact surfaces 406, 506 of first spacer 400 and/or second spacer 500 include one or more features similar to those discussed above configured to couple the respective bone contact surface 406, 506 to shim 700.

In some embodiments, recess 716 is a dovetail joint A cavity 718 is defined in a lower surface 706 between rails 720. Cavity 718 is sized and configured to receive a corresponding dovetail extension 712 extending from a second shim 700. Although embodiments are discussed herein including a dovetail joint, it will be appreciated that the lower surface 706 can define any suitable recess 716 sized and configured to couple to an extension 712 defined by a second shim 700. In some embodiments, the recess 716 is omitted.

In some embodiments, recess 716 is positioned at a proximal edge of lower surface 706, although it will be appreciated that recess 716 can extend through any portion of lower surface 706 such that recess 716 is aligned with an extension 712 on a second shim 700 when multiple shims are aligned. In some embodiments, recess 716 in lower surface 706 is vertically aligned with extension 712 extending from upper surface 704.

FIG. 13 illustrates a first spacer 400 having a first shim 700a and a second shim 700b coupled thereto. First shim 700a and second shim 700b are similar to shim 700 described above in conjunction with FIGS. 16-17, and similar description is not repeated herein. First shim 700a is coupled to first spacer 400. Dovetail extension 712a extending from upper surface 704a of shim 700a is inserted into cavity 442 formed in first spacer 400a. Dovetail extension 712a and channel 442 maintain first shim 700a in a fixed position with respect to first spacer 400a. Second shim 700b is coupled to first shim 700a. Dovetail extension 712b extending from upper surface 704b of second shim 700b is inserted into channel 716a defined by first shim 700a. Dovetail extension 712b and cavity 716a maintain the second shim 700b in a fixed position with respect to first shim 700a and first spacer 400. Although embodiments are illustrated with two shims 700a, 700b, it will be appreciated that any number of shims can be inserted between a first spacer 400 and a second spacer 500.

In some embodiments, each of shims 700a, 700b has a predetermined thickness. For example, in various embodiments, each of shims 700a, 700b can have a predetermined thickness of about 1 mm to about 5 mm, such as, for example, 1 mm, 2 mm, 2.5 mm, 3 mm, 3.5 mm, 4 mm, 5 mm, and/or any other suitable thickness. It will be appreciated that shims 700a, 700b can have a greater and/or less thickness in some embodiments. In some embodiments, each of shims 700a, 700b has a different thickness. For example, in some embodiments, first shim 700a has a first thickness and second shim 700b has a second thickness that is less than, equal to, or greater than the first thickness. A surgeon can select any suitable combination of shims 700a, 700b having similar and/or different thicknesses to correct laxity in joint 12.

Figure 20:
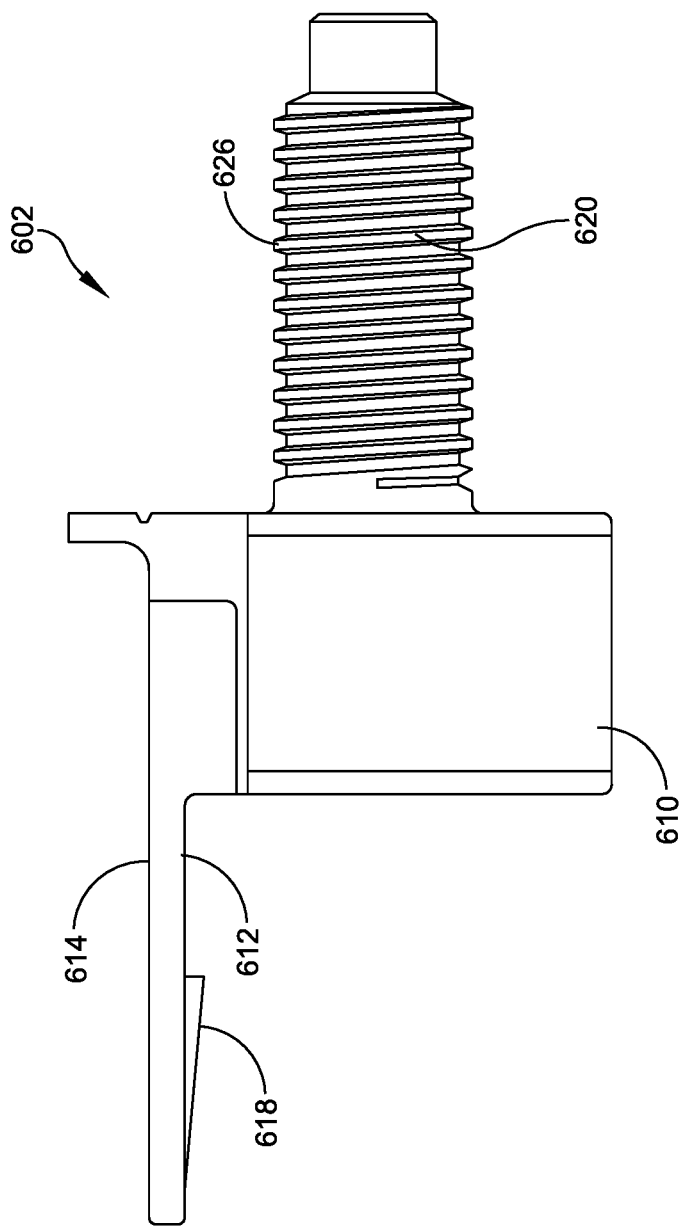
FIG. 20 illustrates a side view of a guide adapter of the resection guide of FIG. 18, in accordance with some embodiments.
Figure 21:
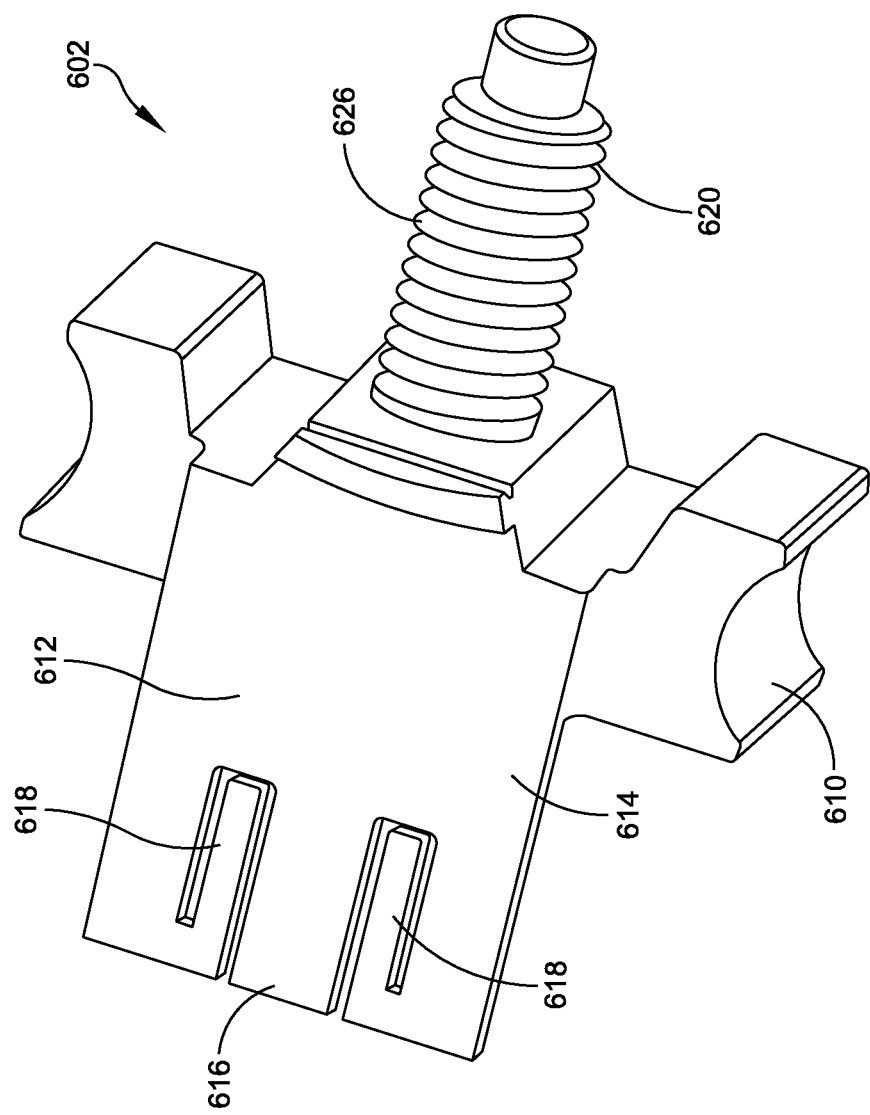
FIG. 21 illustrates a top view of the guide adapter of FIG. 20, in accordance with some embodiments.

FIGS. 18-26 illustrate resection guide 600, in accordance with some embodiments. Resection guide 600 is configured to be coupled to the first spacer 400 and/or the second spacer 500. Resection guide 600 includes a guide adapter 602, an adjustable guide body 604, and an adjustment knob 606. As best shown in FIG. 20, guide adapter 602 includes a body 610 having a flat coupling element 612 and a coupling extension 620 extending from body 610. Flat coupling element 612 includes a substantially flat body 614 sized and configured for insertion into slot 430 formed in first spacer 400. Flat body 614 includes one or more coupling elements 616 configured to maintain guide adapter 602 in a fixed position within slot 430. For example, in some embodiments, coupling elements 616 include leaf-spring elements 618 configured to apply a force to an inner surface of slot 430 to maintain guide adapter 602 in a fixed position with respect to first spacer 400, although it will be appreciated that any suitable coupling element can be used to maintain flat body 614 in the slot 430.

Figure 22:
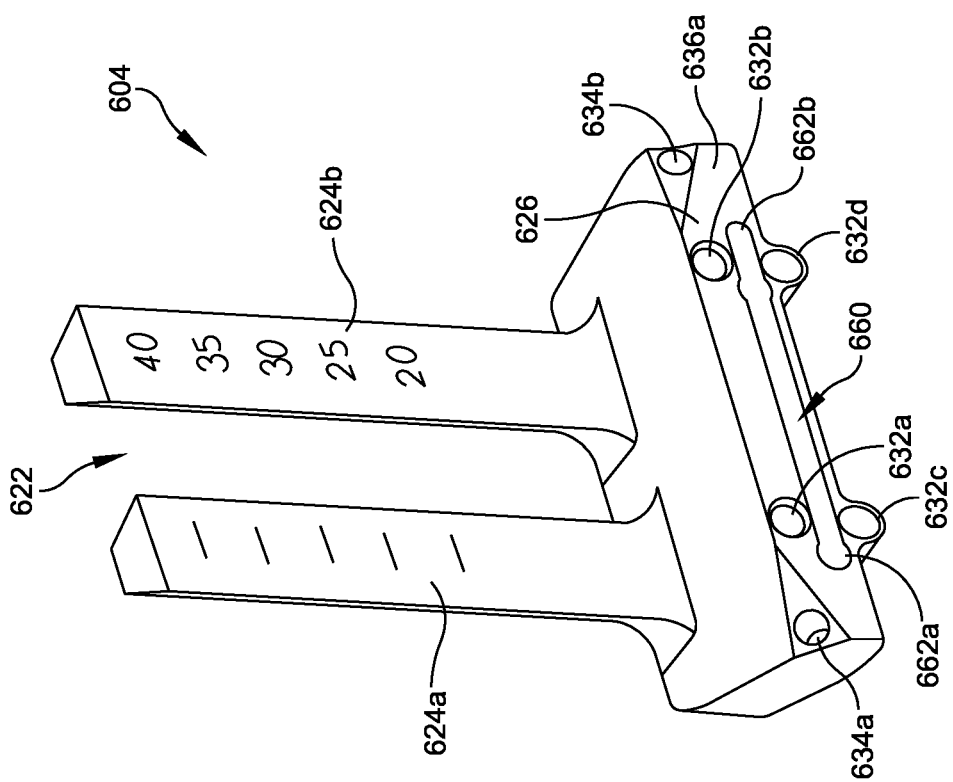
FIG. 22 illustrates an isometric view of a guide body of the adjustable guide of FIG. 18, in accordance with some embodiments.

As best shown in FIGS. 22-24, adjustable guide 604 includes a guide body 626 having a first leg 624a and a second leg 624b extending from a superior edge of the guide body 626. First leg 624a and second leg 624b are spaced apart to define an adjustment slot 622. Adjustment slot 622 is sized and configured to receive a coupling element 620 extending from guide adapter 602. Coupling element 620 is slideable within slot 622 to adjust the vertical position of adjustable guide 604 with respect to first spacer 400. As best shown in FIG. 23, in some embodiments, first leg 624a and/or second leg 624b includes one or more indicators 630 corresponding to a resection depth of a cut to be formed in second bone 16. The resection depth can correspond to a thickness of an implant to be coupled to second bone 16 after forming a resection cut in second bone 16. In some embodiments, coupling element 620 includes one or more threads configured to threadably couple to a locking element 606. Although embodiments are illustrated including a first leg 624a and a second leg 624b, it will be appreciated that one of the legs 624a, 624b can be omitted.

In some embodiments, guide body 626 defines a resection slot 660 extending through body 626 from a proximal surface 636a to a distal surface 636b. Resection slot 660 extends longitudinally from a first end 662a to a second end 662b. The longitudinal profile of resection slot 660 corresponds to a cut profile of a resection to be formed in one or more bones of joint 12, such as second bone 16. Resection slot 660 is sized and configured to receive a cutting tool (e.g., a reciprocating saw or blade) therein. The cutting tool inserted into the resection slot 660 and manipulated to form a resection and/or revision in first bone 14 and/or second bone 16 after positioning adjustable guide 604 in a selected position.

In some embodiments, guide body 626 defines a plurality of first guide holes 632a-632d and a plurality of second guide holes 634a-634b extending therethrough. The guide holes 632a-632d, 634a-634b are each sized and configured to receive a fixation device therethrough. Each fixation device can include any suitable fixation device, such as a k-wire, a screw, and/or a pin, to list only a few possibilities. In some embodiments, the plurality of first fastener holes 632a-632d and the plurality of second fastener holes 634a-634b are sized and configured to receive similar temporary fixation devices, although it will be appreciated that the plurality of first fastener holes 632a-632d and/or the plurality of second fastener holes 634a-634b can be sized and configured to receive different temporary fixation devices.

In some embodiments, each of the plurality of first fastener holes 632a-632d extend from a proximal surface 636a of guide body 626 to a distal surface 636b. First guide holes 632a-632d each extend through guide body 626 along substantially parallel axes. In some embodiments, each of the first guide holes 632a-632d extend through guide body 626 at a first angle with respect to a horizontal axis of guide body 626. In the illustrated embodiment, each of the first guide holes 632a-632d have a hole axis parallel with the horizontal axis of guide body 626, although it will be appreciated that the first guide holes 632a-632d can extend through guide body 626 along a hole axis positioned at an angle with respect to the horizontal axis of guide body 626.

In some embodiments, each of the plurality of second guide holes 634a-634b extend from proximal surface 636a of guide body 626 to distal surface 636b. In some embodiments, each of the second guide holes 634a-634b extend through the guide body 626 at a second angle with respect to the horizontal axis of the guide body 626, different than the first angle. In the illustrated embodiment, each of the second guide holes 634a-634b extend through the guide body 626 along an axis at a second angle between 0 and 90° with respect to the horizontal axis, although it will be appreciated that the second guide holes 634a-634b can extend through the guide body 626 at any suitable angle.

Figure 26:
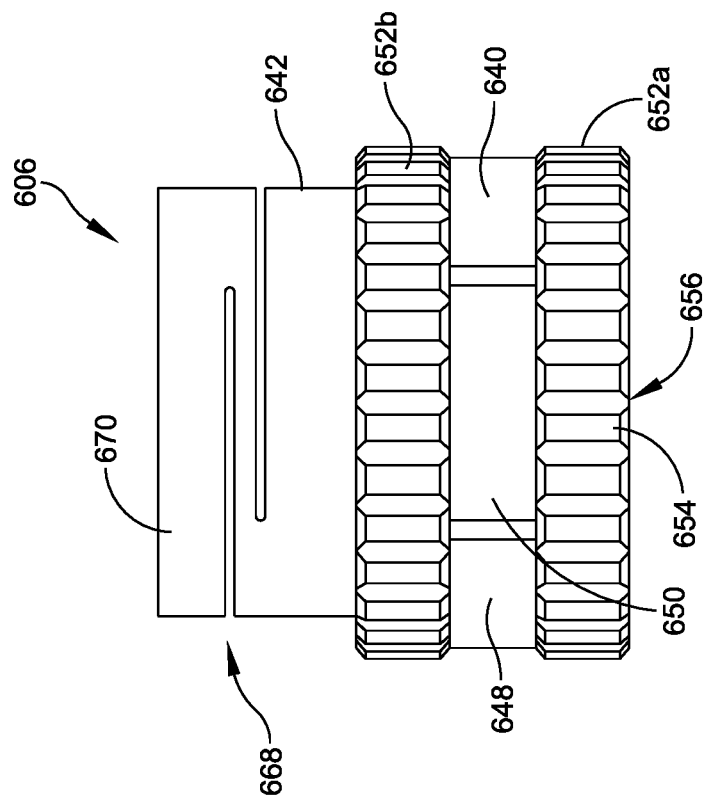
FIG. 26 illustrates a top view of the locking knob of FIG. 25, in accordance with some embodiments.
Figure 25:
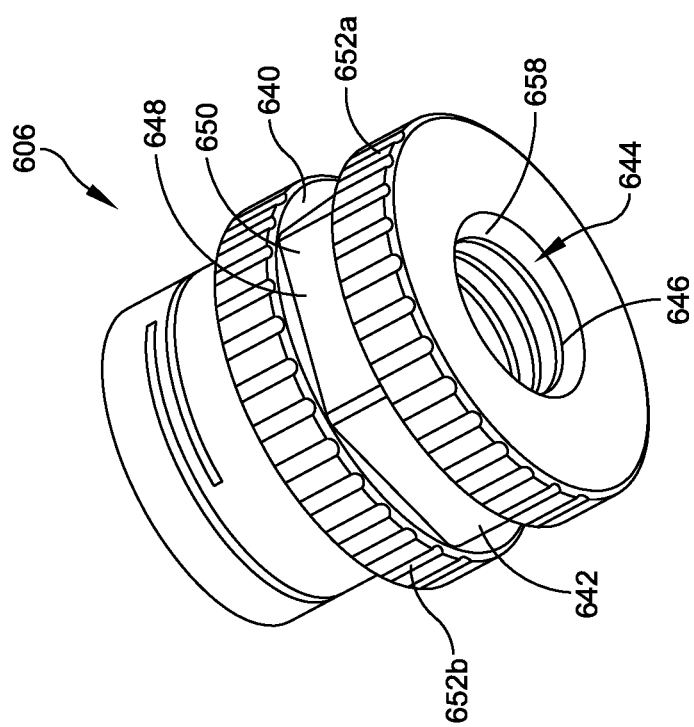
FIG. 25 illustrates an isometric view of a locking knob of the adjustable guide of FIG. 18, in accordance with some embodiments.

As best shown in FIGS. 25-26, in some embodiments, locking element 606 is a locking knob 640 including a body 642 defining a channel 644 extending therethrough. Channel 644 includes one or more mating features 646 configured to couple locking knob 640 to coupling element 620. For example, in embodiments including a thread 626 formed on coupling element 620, mating feature 646 includes a complementary internal thread 658. The locking knob 640 can be threadably engaged with threads 626 of coupling element 620 to advance locking knob 640 onto coupling element 620.

In some embodiments, locking knob 640 includes a tool engagement feature 648. Tool engagement feature 648 is sized and configured to engage with a tool, such as a wrench, to apply a tightening and/or loosening force to locking knob 640. In some embodiments, tool engagement feature 648 includes a coupling surface 650 having a hexagonal cross-sectional surface/plane with each side of the coupling surface 650 defining a flat or planar face 670 configured to provide an interference fit between locking knob 640 and the corresponding hexagonal wrench. Although embodiments are discussed herein including a hexagonal coupling surface, it will be appreciated that any suitable tool engagement feature 648 can be used to couple locking knob 640 to a tool.

In some embodiments, locking knob 640 includes one or more scalloped gripping surfaces 652a-652b. Scalloped gripping surface 652a-652b include a plurality of raised surfaces 654 separated by a plurality of channels 656. The plurality of raised surfaces 654 and/or the plurality of channels 656 provide a textured gripping surface for a user to grip and manipulate locking knob 640. For example, in some embodiments, scalloped gripping surfaces 652-652b allow a user to hand tighten and/or loosen locking knob 640 onto coupling element 620 prior to and/or after engagement of a tool with tool engagement feature 648. Although embodiments are illustrated with two gripping surfaces 652a-652b, it will be appreciated that locking knob 640 can include a lesser and/or greater number of gripping surfaces.

In some embodiments, locking knob 640 is configured to be rotatably coupled to coupling element 620. Locking knob 640 can engaged with threads 626 of coupling element 620 to apply a locking force to adjustable guide 604 to maintain adjustable guide 604 in a fixed position. Locking knob 640 can be loosened and/or partially disengaged from threads 626 to allow vertical adjustment of adjustable guide 604 with respect to guide adapter 602. For example, in some embodiments, coupling element 620 is sized and configured to slide within slot 622 defined by adjustable guide 604. Locking knob 640 can include one or more spiral channels 668 extending about body 642. The spiral channels 668 enable body 642 to be compressed when locking knob 606 is tightened against adjustable guide 604 to increase the force applied to adjustable guide 604. In the illustrated embodiment, spiral channels 668 allow a distal portion 670 of the locking knob 640 to act as a leaf-spring to increase the force applied to the adjustable guide 604.

Although embodiments are discussed herein including a locking knob 640, it will be appreciated that locking element 606 can include any suitable coupling mechanism. For example, in various embodiments, locking element 606 can include one or more of a knob, a lever, a toggle, a ball-detent, and/or any other suitable coupling mechanism.

The spacer assembly 300 and the adjustable guide assembly 600 can be configured for use in a revision surgery. Prior to a revision surgery, a CT or MRI scanned image or series of images is taken of a patient's ankle 12 and then converted from, e.g., a DICOM image format, to a solid computer model of the ankle including the calcaneus, talus, tibia, navicular, and fibula to determine implant alignment, type, and sizing using specialized modeling methods that are often embodied in computer software. The computer model illustrates deformities and/or laxity in the joint 12 that was not corrected by and/or occurred subsequent to a previous primary replacement surgery. The computer model can further illustrate foreign objects coupled to the joint 12, such as implants installed during the primary replacement surgery.

After generating the computer model, a first spacer 400, 400a and a second spacer 500, 500a are generated to match the solid computer model. The spacers 400, 500 can be generated using any suitable method, such as, for example, using a rapid prototyping technique including a processing unit and a rapid prototyping machine, as discussed in greater detail in U.S. Pat. No. 5,768,134, issued on Jun. 16, 1998, entitled "Method for Making a Perfected Medical Model on the Basis of Digital Image Information of a Part of the Body," which is incorporated herein by reference in its entirety. After generating the spacers 400, 500, the joint 12 of the patient can be surgically accessed and one or more of the preexisting primary implants can be removed from the joint 12. In some embodiments, a conversion instrument 200 can be used to form one or more additional revision cuts in one of first bone 14 or second bone 16.

Figure 27:
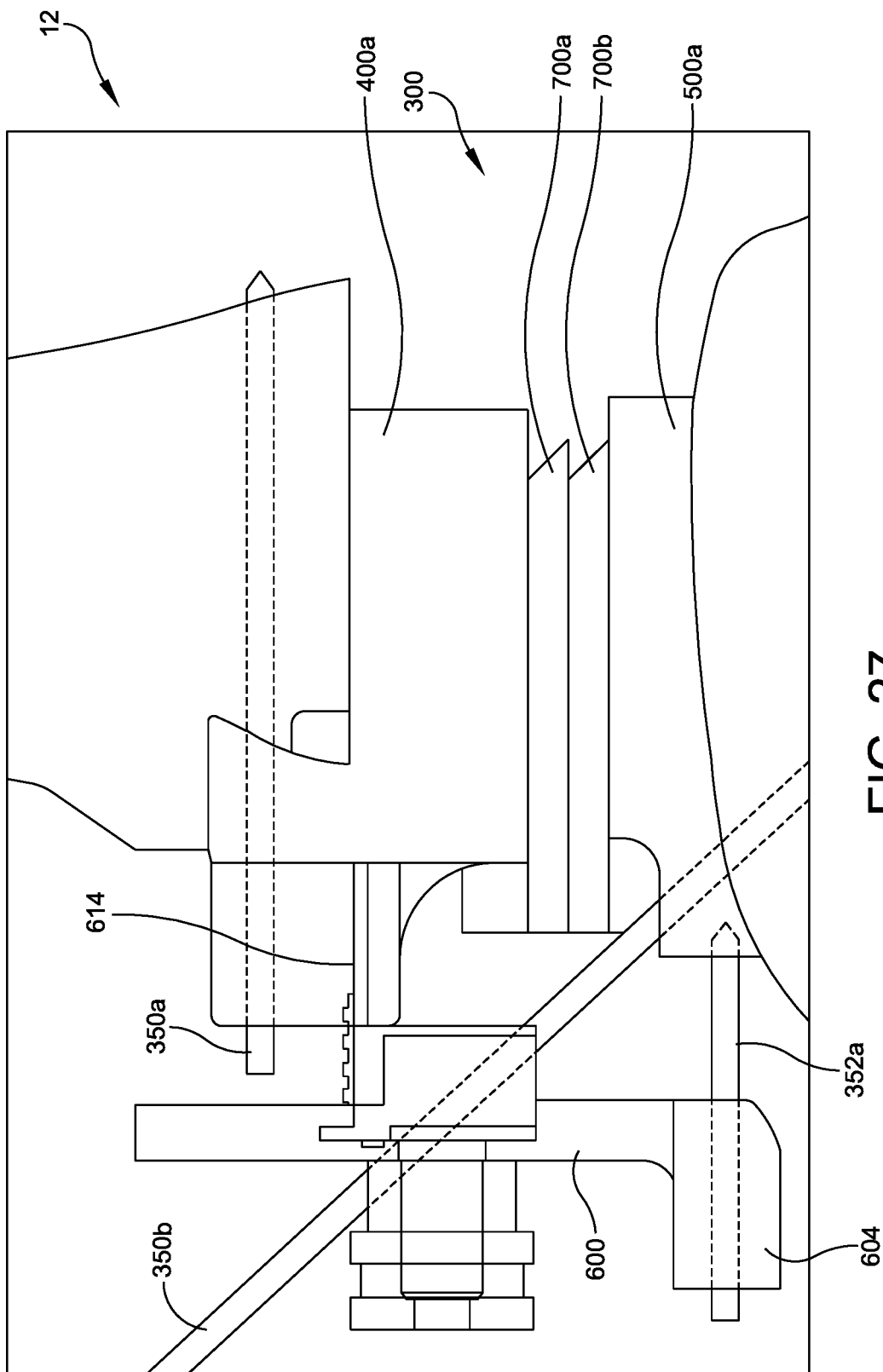
FIG. 27 illustrates the spacer assembly of FIG. 6 having one or more guide elements inserted through an adjustable guide assembly, in accordance with some embodiments.

After resection of first bone 14 and/or second bone 16 and/or removal of one or more implants from joint 12, the first spacer 400, 400*a* and the second spacer 500, 500*a* are positioned within the joint space to position the first and second bones 14, 16 in a pre-operatively planned corrected position. The first spacer 400, 400*a* is positioned within the resection formed in the first bone 14. The first spacer 400, 400*a* can be manipulated until one or more of the bone contact surfaces 404, 414*a* securely engage with the topography of the first bone 14. As shown in FIG. 27, with the first spacer 400*a* engaged with the first bone, one or more temporary fixation devices 350*a*, such as k-wires, are inserted through one or more of the fixation holes 416*a*-416*b*, 428*a*-428*b* to temporarily anchor the first spacer 400*a* to the first bone 14. The second spacer 500, 500*a* is positioned in contact with the second bone 16. For example, the second spacer 500, 500*a* can be manipulated until a bone contact surface 504 securely engages with the topography of the second bone 16. With the second spacer 500, 500*a* securely engaged with the second bone 16, one or more temporary fixation devices 350*b*, such as k-wires, are inserted through one or more of the fixation holes 514*a*-514*b* to temporarily anchor the second spacer 500, 500*a* to the second bone 16.

With further reference to FIG. 27, a coupling surface 406 of first spacer 400*a* is positioned in an abutting relationship with a coupling surface 506 of second spacer 500*a*. Mating element 512 extending from coupling surface 506 of second spacer 500*a* is inserted into recess 422 formed in coupling surface 406. First spacer 400*a* and second spacer 500*a* position first bone 14 and second bone 16 in a predetermined position with respect to one or more of a varus/valgus orientation, a flexion/extension orientation, an inversion/eversion orientation, an anterior/posterior position, a medial/lateral position, and/or a proximal/distal position. In some embodiments, mating element 512 and recess 422 constrain one or more degrees of freedom of joint 12 (such as medial/lateral position, proximal/distal position, flexion/extension orientation, etc.) while allowing adjustment of one or more other degrees of freedom (such as inversion/eversion orientation, anterior/posterior position, etc.). In some embodiments, the first guide 400*a* and/or the second guide 500*a* include one or more features configured to verify an alignment and/or position of the respective guide 400*a*, 500*a*, such as through fluoroscopy.

After positioning the first spacer 400*a* and/or the second spacer 500*a* in the joint space 12, one or more shims 700*a*, 700*b* can be coupled to the first spacer 400*a* and/or the second spacer 500*a* to correct laxity in the joint 12. For example, in the illustrated embodiment, a first shim 700*a* is coupled to a coupling surface 406 of the first spacer 400*a* and a second shim 700*b* is coupled to the first shim 700*a*. The second shim 700*b* abuts and couples to the coupling surface 506 of second spacer 500*a*. The number and/or thickness of shims 700*a*, 700*b* can be selected intraoperatively to correct pre-existing laxity and/or intraoperatively generated laxity in joint 12.

The surgeon then couples adjustable guide 600 to one of the first spacer 400 and/or second spacer 500. In the illustrated embodiments, the adjustable guide 600 is coupled to first spacer 400. The coupling extension 620 of the guide adapter 602 is slideably engaged with the slot 430 formed in the first spacer 400. Leaf-spring elements 618 apply a force to an inner surface of slot 430 to maintain the guide adapter 602 in a fixed position with respect to first spacer 400. The adjustable guide 604 is coupled to the guide adapter 602 by inserting the coupling element 620 of the guide adapter 602 into slot 622 defined by the adjustable guide 604. The locking knob 606 is threadably engaged with the coupling element 620 to lock the adjustable guide 604 to the guide adapter 602.

The surgeon adjusts the vertical position of adjustable guide 604 by loosening locking knob 606 and sliding adjustable guide 604 up/down to adjust a corresponding resection depth of a cut to be formed in the second bone 16. The position of adjustable guide 604 can be viewed using fluoroscopy. A k-wire, saw blade, and/or other element can be inserted at the desired resection location to visualize the resection and to determine the appropriate resection depth intraoperatively.

Figure 28:
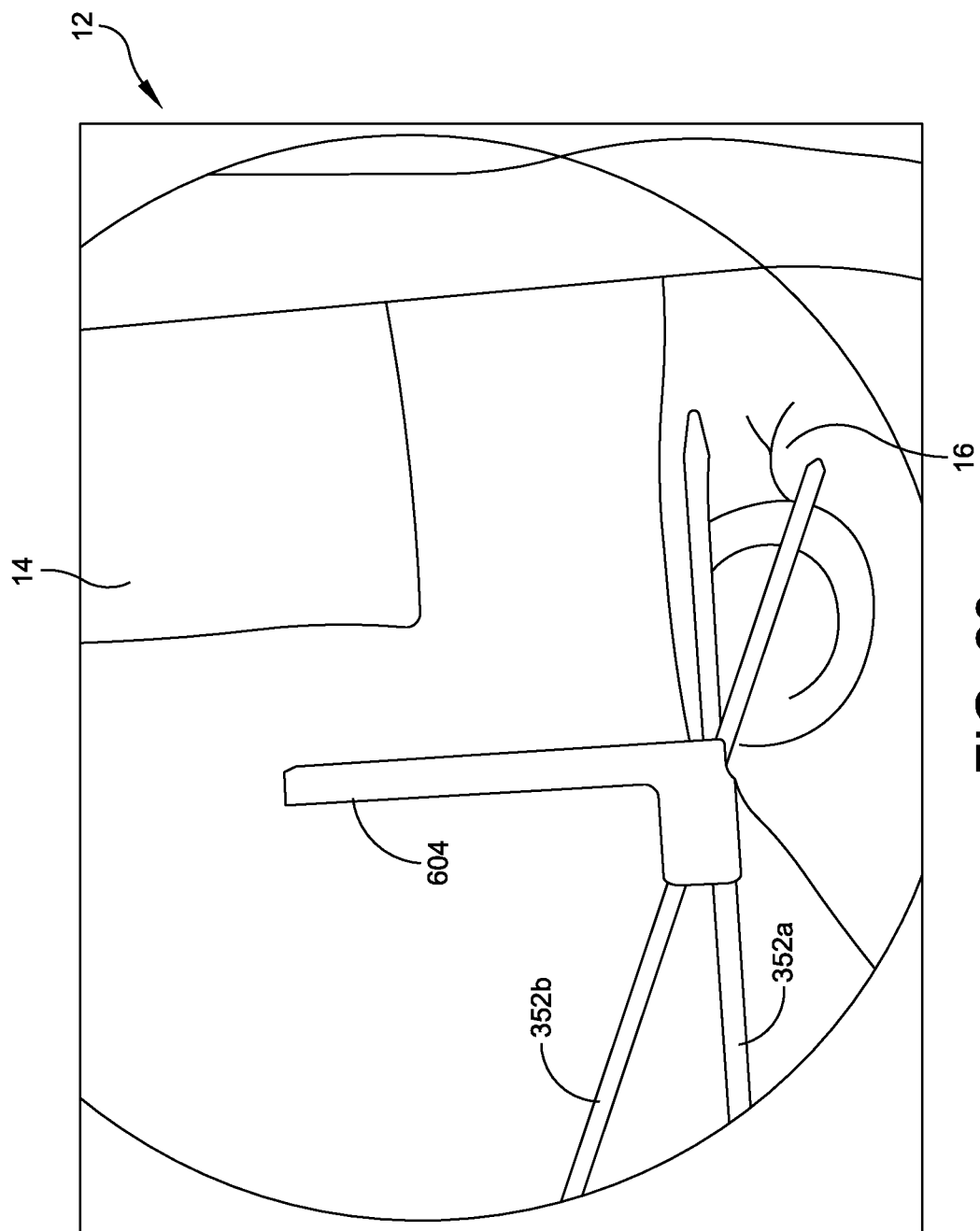
FIG. 28 illustrates the guide body of FIG. 22 coupled to a first guide element and a second guide element, in accordance with some embodiments.

In some embodiments, markings on adjustable guide 604 indicate the distance of the resection cut in second bone 16 from a resection cut in first bone 14. The first leg 624*a* and/or the second leg 624*b* of adjustable guide 604 include one or more depth markings to provide a visual indication to the surgeon regarding the depth of the resection cut. The depth of the resection can be further influenced by the thickness of an implant to be coupled to second bone 16. After selecting a desired resection cut depth, locking element 606 is tightened to fix the position of adjustable guide 604. As shown in FIGS. 27-28, one or more guide elements 352*a*-352*b*, such as guide pins, are inserted through one or more of the first guide holes 632*a*-632*d* and/or second guide holes 634*a*-634*b* formed through guide body 626.

After inserting the guide pins, the spacer assembly 300 and all fixation elements, except the guide element 352*a*-352*b*, are removed from the joint 12. The guide body 626 is re-positioned with respect to the second bone 16 by sliding the guide elements 352*a*-352*b* through first guide holes 632*a*-632*d* and/or second guide holes 634*a*-634*b*, as shown in FIG. 28. A resection cut is formed in second bone 16 by inserting a cutting instrument through resection slot 660 defined by the guide body. In some embodiments, a separate resection cut guide can be coupled to second bone 16 by engaging the resection cut guide with the temporary guide elements in second bone 16. Removal of spacer assembly 300 prevents a resecting cut from intersecting the spacers and further allows the resection guide body 626 to be positioned closer to the second bone 16. Additional fixation elements, such as k-wires or guide pins, may be inserted through one or more of fixation holes 634*a*-634*b* to further fix the position of guide body 626 with respect to the second bone 16.

If adjustment of the resection depth is necessary, the guide body 626 can be adjusted by repositioning the guide pins into an alternative set of guide holes 632*a*-632*d*. For example, in some embodiments, a first set of guide holes 632*a*, 632*b* is positioned above a second set of guide holes 632*c*, 632*d*. The first and second sets of guide holes 632*a*-632*d* allow adjustment of the resection depth by a predetermined amount, for example, a predetermined amount in the range of +/−0-5 mm, such as 0.5 mm, 1 mm, 1.5 mm, 2 mm, 2.5 mm, 3 mm, 3.5 mm, 4 mm, 4.5 mm, and/or 5 mm. It will be appreciated that guide holes 632*a*-632*d* can have a greater and/or lesser spacing allowing any predetermined amount of adjustment.

After fixing the position of guide body 626, second bone 16 is resected. Guide body 626, guide elements 352*a*-352*b*, and/or other elements are removed from second bone 16. The resected space between first bone 14 and second bone 16 is cleared of all resected bone down to the level of the resection cut, such as a flat cut in second bone 16.

Figure 29:
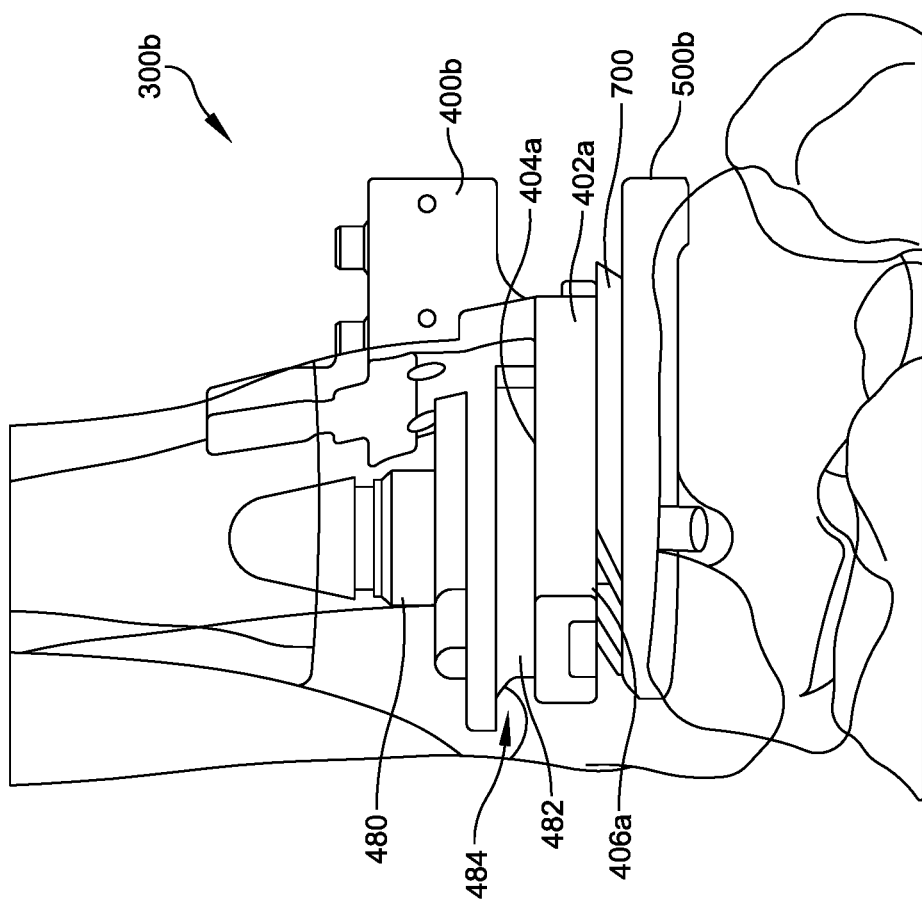
FIG. 29 illustrates a spacer assembly including a first spacer configured to be coupled to an implant installed in a first bone, in accordance with some embodiments
Figure 30:
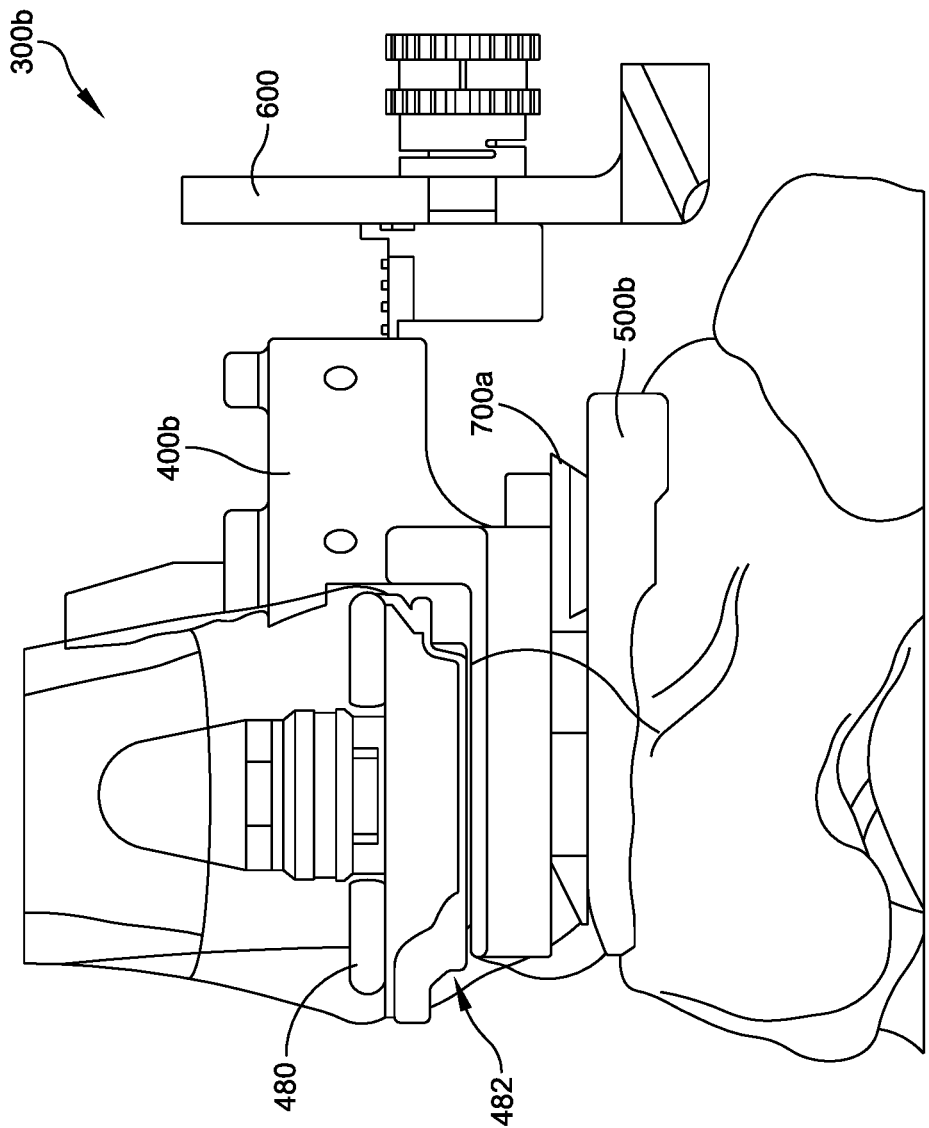
FIG. 30 illustrates the spacer assembly of FIG. 29 having an adjustable guide coupled thereto, in accordance with some embodiments.

FIGS. 29-30 illustrate an alternative embodiment of a spacer assembly 300b including a first spacer 400b configured to be coupled to an implant 480 installed in first bone 14, in accordance with some embodiments. The spacer assembly 300b is similar to the spacer assembly 300 discussed above in conjunction with FIGS. 6-9, and similar description is not repeated herein. The spacer assembly 300a includes a first spacer 400b and a second spacer 500b configured to position the first bone 14 and the second bone 16 in a corrected alignment. In some embodiments, the corrected alignment of joint 12 corresponds to a preoperatively planned deformity correction that is planned based on anatomic references and/or surgeon preferences. First spacer 400b and/or second spacer 500b set one or more degrees of freedom of joint 12. For example, in various embodiments, the spacer assembly 300b can correct one or more of a varus/valgus orientation, a flexion/extension orientation, an inversion/eversion orientation, an anterior/posterior position, a medial/lateral position, and/or a proximal/distal position between the first bone 14 and the second bone 16 intraoperatively.

First spacer 400b includes a body 402a extending between upper surface 404a and a lower surface 406a. The upper surface 404a defines a planar surface. An implant coupling element 482 extends from the upper surface 404a. The implant coupling element 482 is sized and configured to be received within a lock detail 484 defined by an implant 480 coupled to the first bone 14. The implant 480 can include any suitable implant, such an articulation implant coupled to the first bone 14 during a previous joint replacement surgery and/or implanted concurrently with a current ankle replacement/revision surgery.

Figure 31:
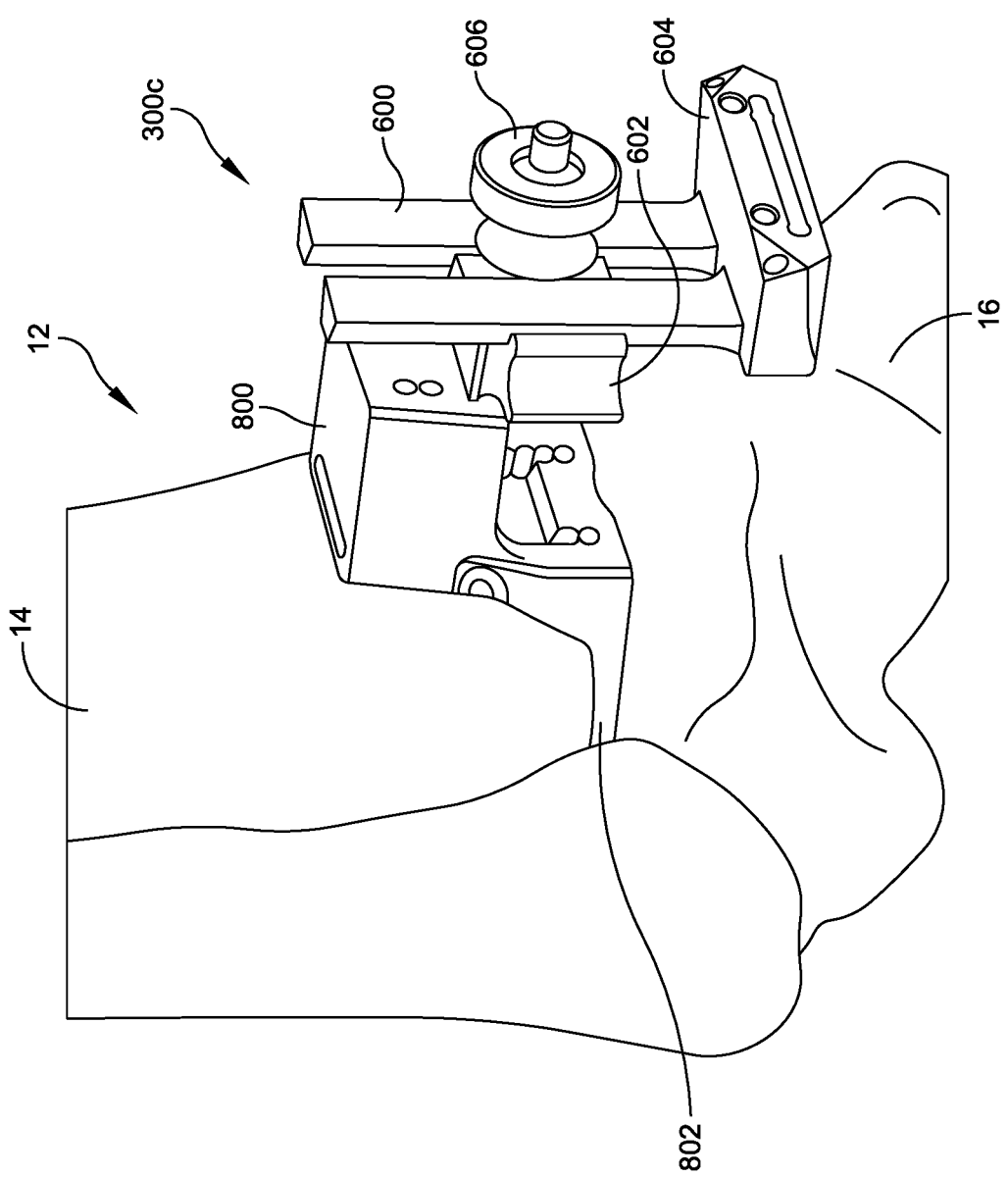
FIG. 31 illustrates a spacer assembly including a monolithic spacer, in accordance with some embodiments.
Figure 32:
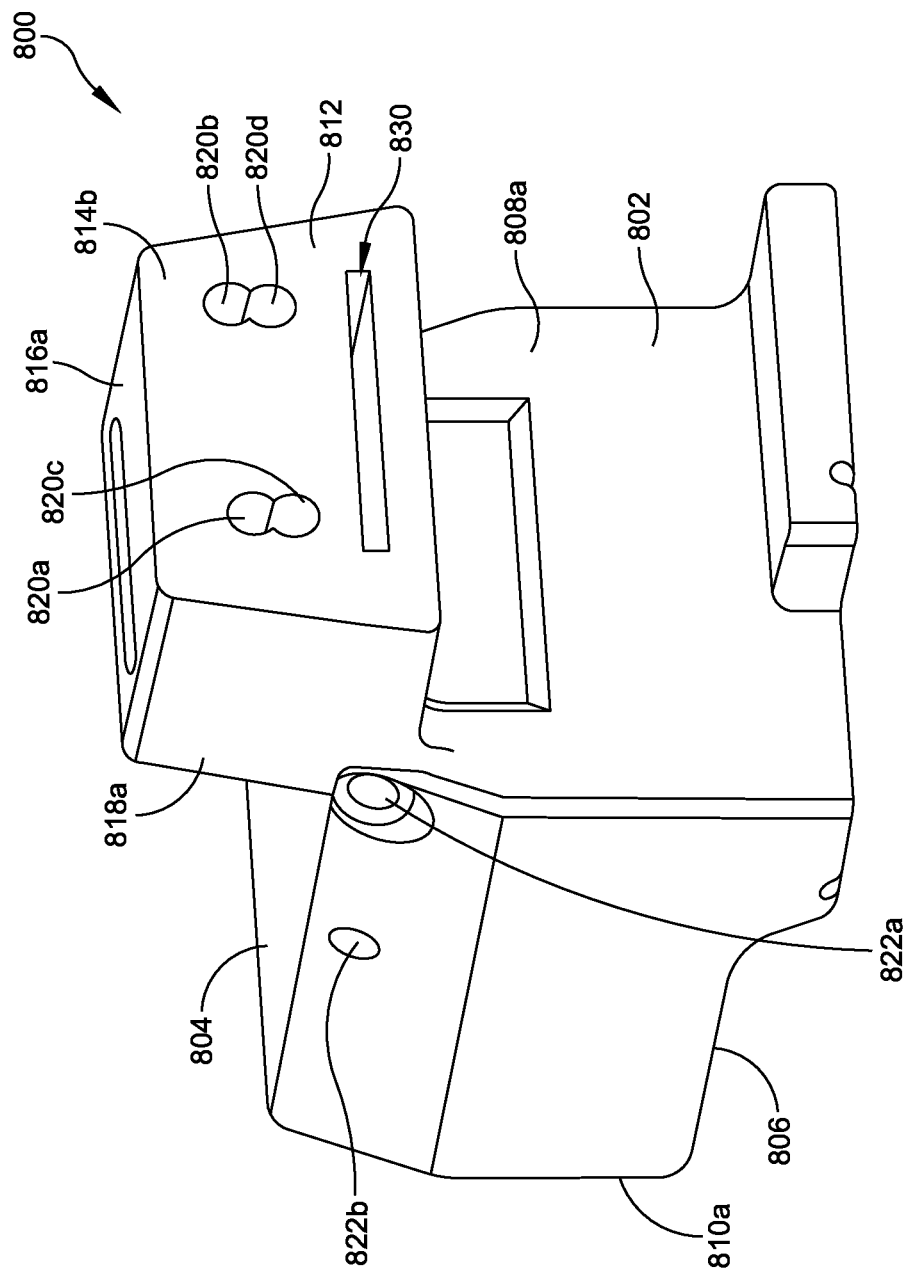
FIG. 32 illustrates an isometric view of the monolithic spacer of FIG. 31, in accordance with some embodiments.
Figure 33:
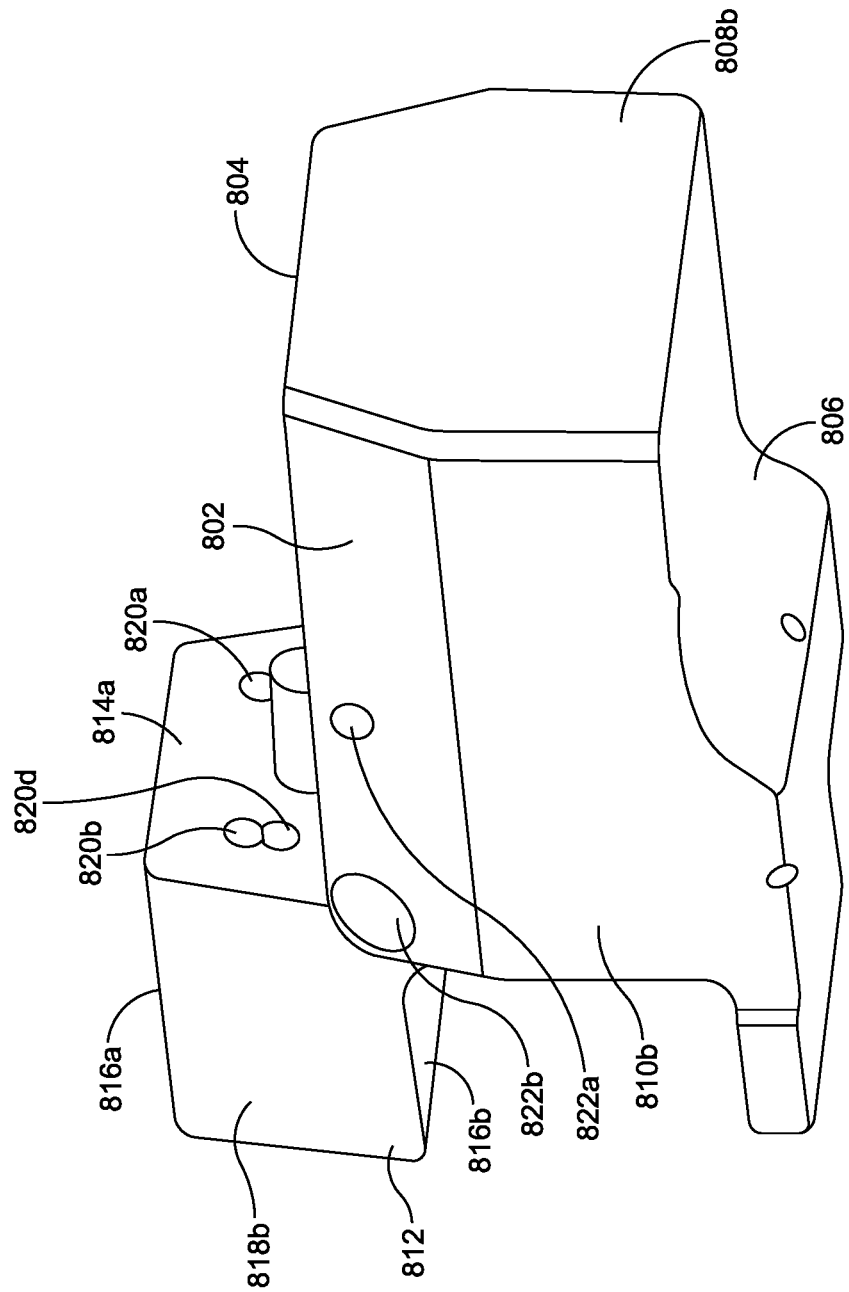
FIG. 33 illustrates a rear view of the monolithic spacer of FIG. 32, in accordance with some embodiments.

FIGS. 31-33 illustrate an alternative embodiment of a spacer assembly 300c including a monolithic spacer 800, in accordance with some embodiments. The spacer assembly 300c is similar to the spacer assembly 300 discussed above, and similar description is not repeated herein. The spacer assembly 300c includes a monolithic spacer 800 configured to position the first bone 14 and the second bone 16 in a corrected alignment. In some embodiments, the corrected alignment of joint 12 corresponds to a preoperatively planned deformity correction that is planned based on anatomic references and/or surgeon preferences. Monolithic spacer 800 sets one or more degrees of freedom of joint 12. For example, in various embodiments, the monolithic spacer 800 can correct one or more of a varus/valgus orientation, a flexion/extension orientation, an inversion/eversion orientation, an anterior/posterior position, a medial/lateral position, and/or a proximal/distal position between the first bone 14 and the second bone 16 intraoperatively.

As best shown in FIGS. 32-33, monolithic spacer 800 includes a body 802 having a thickness extending between a first bone contacting surface 804 and a second bone contacting surface 806. Body 802 further extends longitudinally between a proximal surface 808a and a distal surface 808b and has a width extending between a first side surface 810a and a second side surface 810b. First bone contacting surface 804 is configured to abut a surface of first bone 14 and second bone contacting surface 806 is configured to abut a surface of the second bone 16, such as a superior portion of a talus. In some embodiments, bone contact surfaces 804, 806 are configured to engage a previously resected bone surface of respective first bone 14 or second bone 16 and/or define patient-specific profiles configured to surface match respective first bone 14 and/or second bone 16. For example, first bone contacting surface 804 can be configured to engage a previously resected surface of first bone 14 and second bone contacting surface 806 can be configured to interface with existing bony anatomy and/or cartilage or other soft tissue of second bone 16.

In some embodiments, monolithic spacer 800 includes a bone engaging structure 812 coupled to a proximal surface 808a of body 802. Bone engaging structure 812 extends superiorly from the proximal surface 808a terminating above first bone contacting surface 804. Bone engaging structure 812 extends between a bone contacting surface 814a and an opposing surface 814b, an upper surface 816a and a lower surface 816b, and first and second side surfaces 818a, 818b. In some embodiments, the bone contacting surface 814a includes a patient-specific profile configured to surface-match a portion of first bone 14, such as an anterior surface of a tibia, for example. Bone engaging structure 812 is configured to maintain monolithic spacer 800 in a fixed anterior/posterior position with respect to first bone 14. Bone engaging structure 812 defines a slot 830 extending from opposing surface 814b at least partially into bone engaging structure 812. In some embodiments, slot 830 extends from opposing surface 814b to bone contacting surface 814a. Slot 830 is sized and configured to receive a flat body 614 of resection guide 600 therein.

In some embodiments, monolithic spacer 800 includes a plurality of first fixation holes 820a-820d extending from opposing surface 814b to bone contacting surface 814a. The one or more fixation holes 820a-820d are sized and configured to receive a fixation element therethrough. The fixation elements can include any suitable fixation element, such as a k-wire, screw, pin, and/or any other suitable fixation element. The fixation elements are configured to maintain monolithic spacer 800 in a fixed position with respect to first bone 14 and/or second bone 16. In some embodiments, the fixation holes 820a-820d are parallel, although it will be appreciated that two or more of fixation holes 820a-820d can have non-parallel axes.

In some embodiments, monolithic spacer 800 includes a plurality of second fixation holes 822a-822b extending from one of a first side wall 810a or a second side wall 810b of body 802 to the other of the first side wall 810a or the second side wall 810b. The fixation holes 822a-822b are angled with respect to first and second side surfaces 810a, 810b such a first side of each of the fixation holes 822a-822b is positioned proximally of a second side. In some embodiments, fixation holes 822a-822b extend through body 802 along intersecting hole axis, although it will be appreciated that the fixation holes 822a-822b can extend through the body 802 along non-intersecting hole axis in some embodiments.

In some embodiments, a kit can include multiple monolithic spacers each having a different thickness. For example, in some embodiments, a kit can include a first monolithic spacer having a first thickness between a first bone contact surface 804 and a second bone contact surface 806 and a second monolithic spacer having a second thickness between a first bone contact surface 804 and a second bone contact surface 806. The second thickness can be greater than the first thickness. A surgeon can select one of the first monolithic spacer or the second monolithic spacer based on laxity between first bone 14 and second bone 16. Although embodiments are discussed using two monolithic spacers, it will be appreciated that any number of monolithic spacers having any number of thicknesses can be included, and are within the scope of this disclosure.

Figure 34:
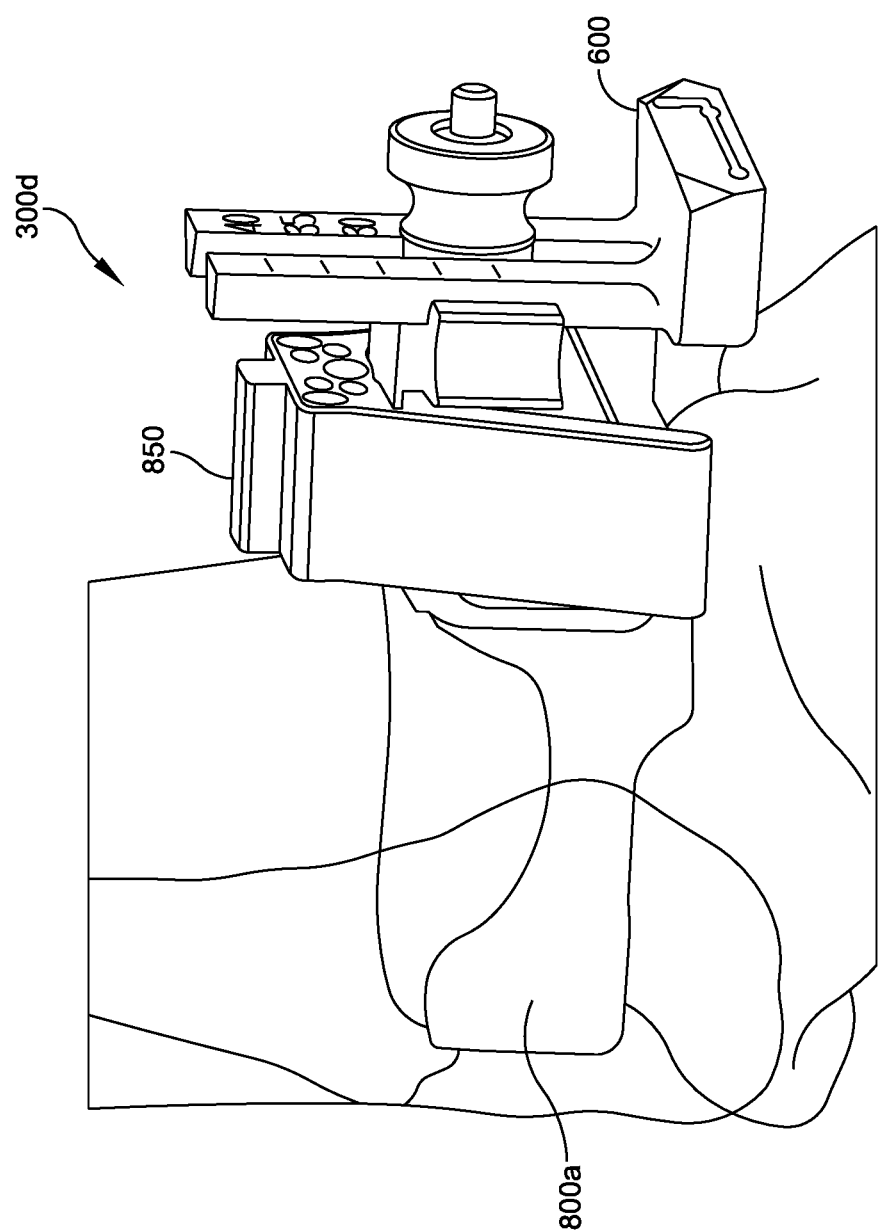
FIG. 34 illustrates a spacer assembly including a monolithic spacer and a cutting guide coupled thereto, in accordance with some embodiments.
Figure 35:
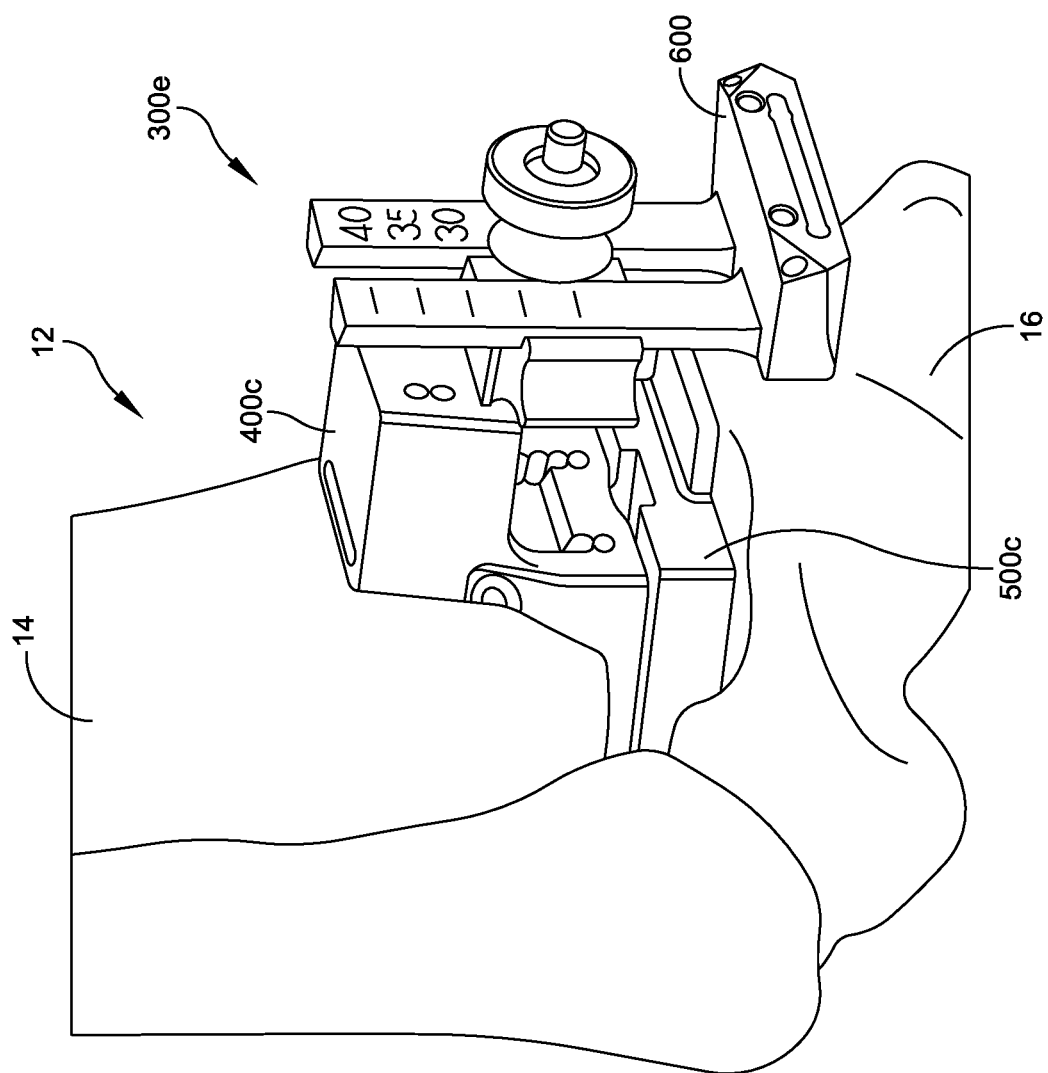
FIG. 35 illustrates a spacer assembly including a first spacer and a second spacer coupled in a telescoping arrangement, in accordance with some embodiments.
Figure 36:
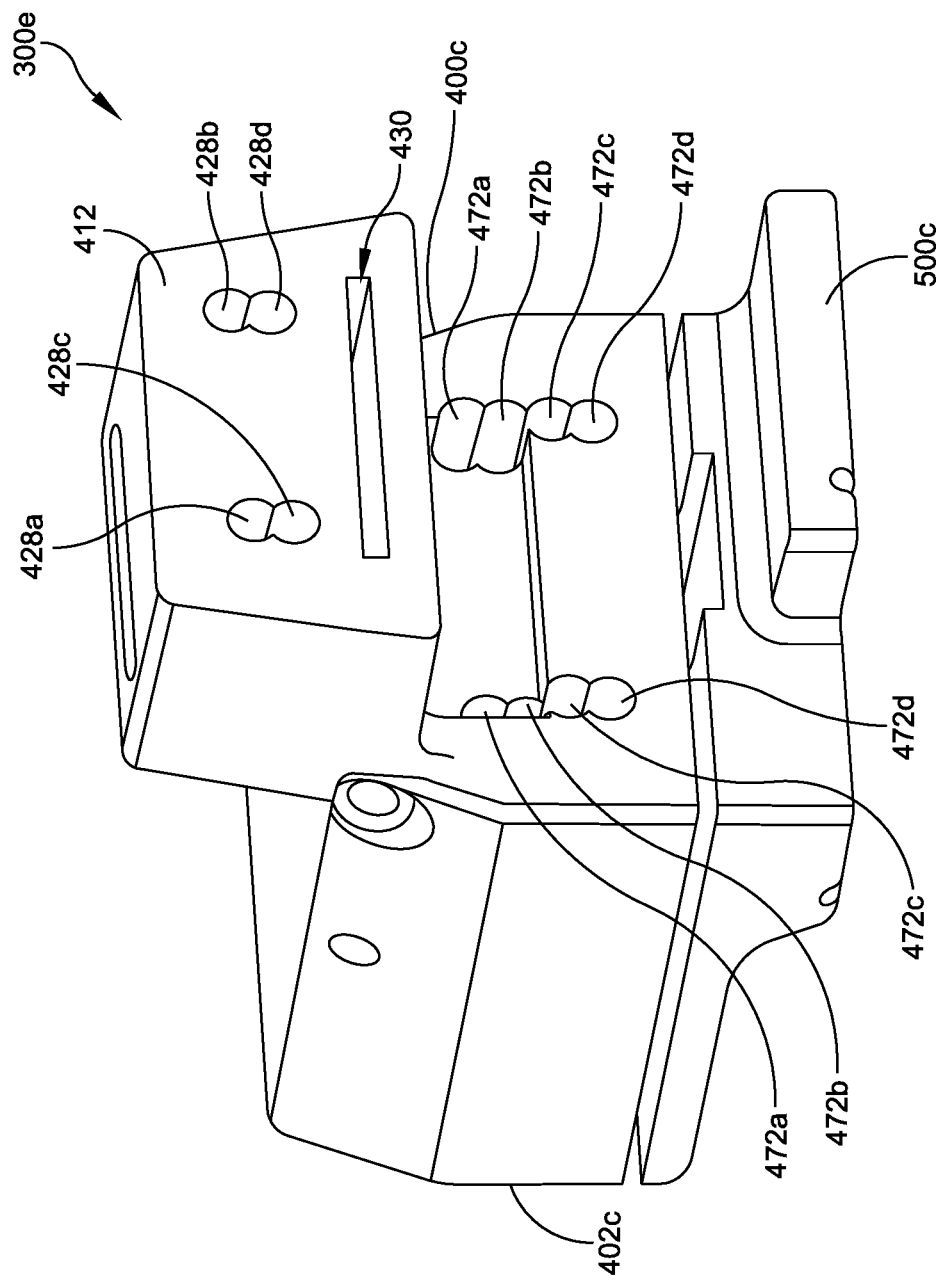
FIG. 36 illustrates an isometric view of a first spacer and a second spacer coupled in a telescoping arrangement, in accordance with some embodiments.

FIG. 34 illustrates a patient-specific spacer assembly 300d including a monolithic spacer 800a having a cutting guide 850 coupled thereto, in accordance with some embodiments.

The cutting guide 850 is similar to the guide 250 discussed above in conjunction with FIG. 3, and similar description is not repeated herein. In some embodiments, the cutting guide 850 is configured to guide a cutting instrument for forming one or more cuts in first bone 14 and/or second bone 16. Cutting guide 850 can define a slot 860 sized and configured to receive a coupling extension 620 of an adjustable guide 600 therein.

FIGS. 35-38 illustrates a spacer assembly 300e including a first spacer 400c and a second spacer 500c having a telescoping connection therebetween, in accordance with some embodiments. The spacer assembly 300e is similar to the spacer assembly 300 discussed above, and similar description is not repeated herein.

Figure 37:
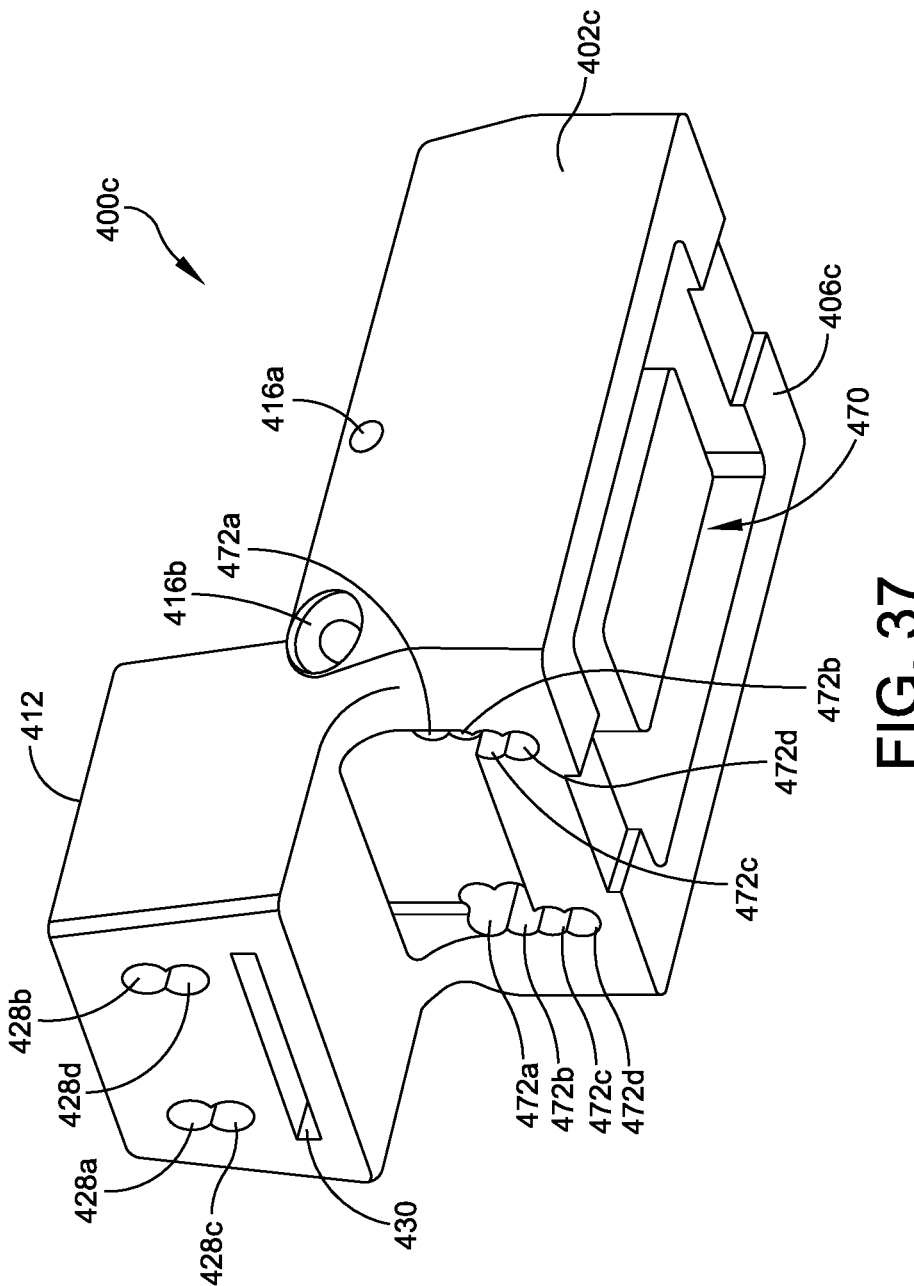
FIG. 37 illustrates a first spacer of the spacer assembly of FIG. 36, in accordance with some embodiments.
Figure 38:
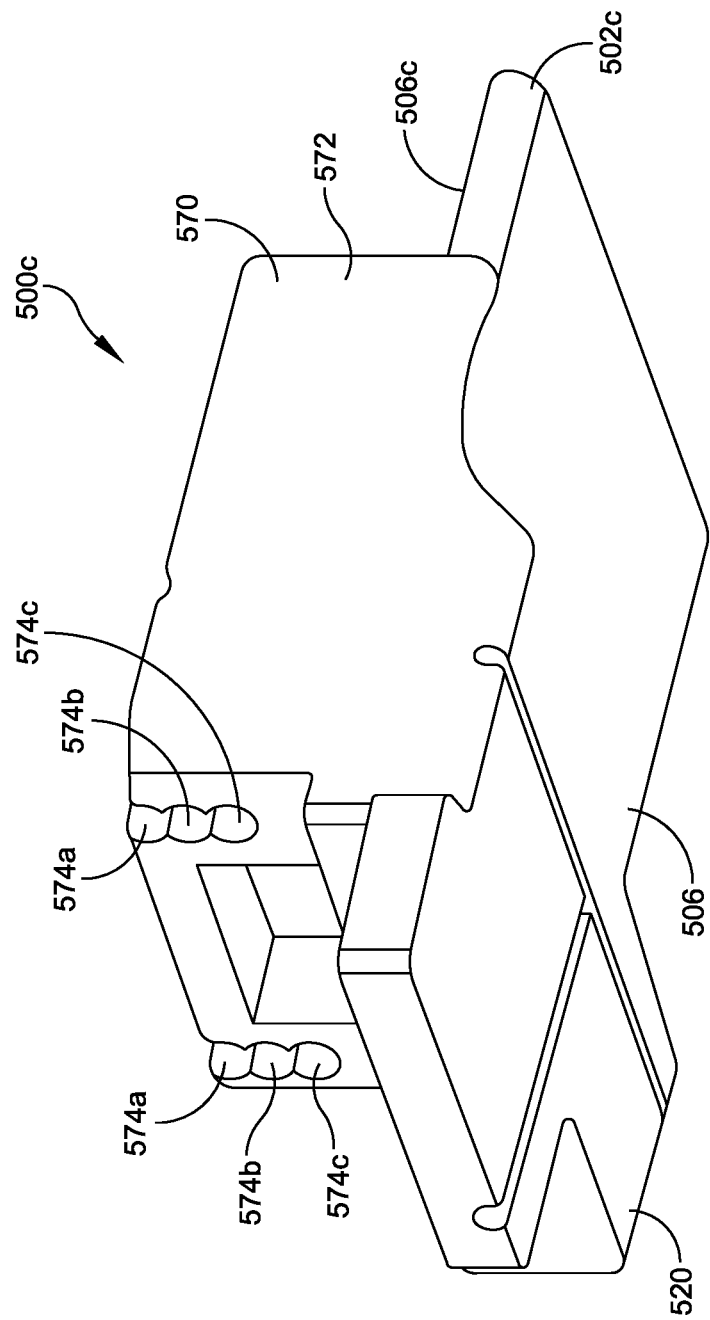
FIG. 38 illustrates a second spacer of the spacer assembly of FIG. 36, in accordance with some embodiments.

In some embodiments, first spacer 400c and second spacer 500c are configured to engage one another via a telescoping connection. For example, first spacer 400c includes a body 402c defining a channel 470 extending from lower surface 406c into body 402c as best seen in FIG. 37. Channel 470 can be a closed and/or open channel having any suitable shape, such as a closed geometric shape (e.g., cylindrical, square, etc.), an open shape, and/or any other suitable shape. For example, in the illustrated embodiment, channel 470 defines a closed square shape extending about the periphery of lower surface 406a, although it will be appreciated that channel 470 can have any suitable shape.

In some embodiments, a plurality of height adjustment holes 472a-472d extend through body 402a from a proximal surface 408a into channel 470. The height adjustment holes 472a-472d are sized and configured to receive a fixation device therein, such as, for example, a k-wire, a pin, a screw, and/or any other suitable fixation device. Although embodiments are illustrated having four sets of height adjustment holes 472a-472d, it will be appreciated that body 402a can define any number of height adjustment holes 472a-472d extending from any of the surfaces of body 402a into channel 470.

In some embodiments, second spacer 500c includes an adjustment body 570 extending from upper surface 506c. Adjustment body 570 extends a predetermined height above upper surface 506c. Adjustment body 570 includes a perimeter wall 572 defining a hollow interior 574. Adjustment body 570 is sized and configured for insertion into channel 470 formed in first spacer 400a. For example, in some embodiments, perimeter wall 572 defines a closed shape corresponding to the closed shape of channel 470. In other embodiments, perimeter wall 572 defines an open shape corresponding to a portion of channel 470. Perimeter wall 572 can extend a predetermined height above the upper surface 506a that is less than, equal to, or greater than a depth of channel 470.

In some embodiments, perimeter wall 572 defines a plurality of height adjustment holes 574a-574c extending from a proximal surface 578 to hollow interior 574. The height adjustment holes 574a-574c are configured to receive a fixation device therein, such as a k-wire, a pin, a screw, and/or any other suitable fixation device. In some embodiments, height adjustment holes 574a-574c have a spacing similar and/or identical to the spacing of height adjustment holes 472a-472d formed in first spacer 400c, although it will be appreciated that height adjustment holes 574a-574c can have a greater and/or lesser spacing than height adjustment holes 472a-472d.

In use, adjustment body 570 is configured to be inserted into channel 470 to couple first spacer 400c to second spacer 500c. First spacer 400c and second spacer 500c define a minimum spacing when adjustment body 570 is fully inserted into channel 470. For example, in some embodiments, adjustment body 570 is inserted into channel 470 until an upper surface of the perimeter wall 572 contacts an inner surface 476 of channel 470, although it will be appreciated that the adjustment body 570 and/or the channel 470 can be tapered such that the upper surface of the perimeter wall 572 does not contact the inner surface 476 of the channel 470 when fully inserted. If laxity is observed in joint 12, the distance between first spacer 400c and second spacer 500c can be increased.

In some embodiments, a distance between first spacer 400c and second spacer 500c can be adjusted by sliding a portion of adjustment body 570 out of channel 470 to increase the distance between first spacer 400c and second spacer 500c. Adjustment body 570 can be adjusted from a minimum spacing (in which the adjustment body 570 has a maximum portion located within the cavity 470) to a maximum spacing (in which the adjustment body 570 has a minimum portion located within the cavity 470). In various embodiments, the spacing can be adjusted continuously and/or discretely from the minimum spacing to the maximum spacing.

In some embodiments, a selected spacing of first spacer 400c and second spacer 500c is maintained by one or more fixation devices. First spacer 400c defines a first plurality of height adjustment holes 472a-472d and second spacer 500c defines a second plurality of height adjustment holes 574a-574c. The position of each of height adjustment holes 472a-472d, 574a-574c is selected such that at least one set of the first plurality of adjustment holes 472a-472d is aligned with at least one set of the second plurality of adjustment holes 574a-574c when first spacer 400c and second spacer 500c are positioned at one or more predetermined distances. A fixation element (not shown), such as a pin, can be inserted through one of the first plurality of adjustment holes 472a-472d and at least partially into a corresponding (i.e., aligned) one of the second plurality of adjustment holes 574a-574c to maintain first spacer 400c and second spacer 500c in a selected spacing. In some embodiments, a fixation element is inserted through each adjustment hole in a pair of aligned adjustment holes 472a-472d, 574a-574c.

Figure 39:
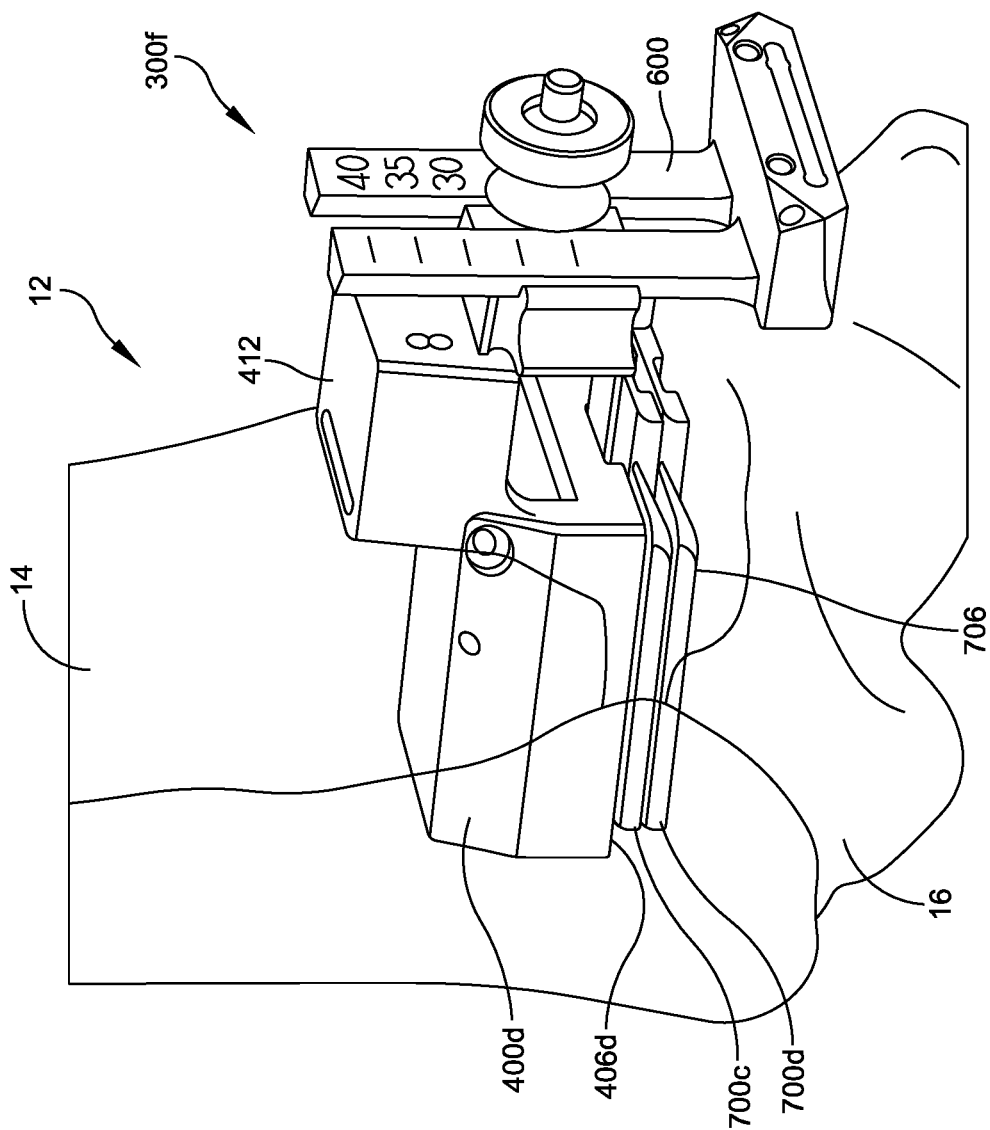
FIG. 39 illustrates an isometric view of a spacer assembly including a first spacer and one or more shims configured to abut a second bone of a joint, in accordance with some embodiments.

FIG. 39 illustrates a spacer assembly 300f including a first spacer 400d and one or more shims 700c, 700d, in accordance with some embodiments. First spacer 400d is similar to first spacer 400 discussed above and shims 700c, 700d are similar to shim 700 described above, and similar description is not repeated herein. In some embodiments, coupling surface 406d of the first spacer 400d and/or a lower surface 706 of the shims 700c, 700d are configured to directly contact a surface of second bone 16. In some embodiments, coupling surface 406d and/or the lower surface 706 of each of the shims 700c, 700d defines a planar surface configured to interact with a partially and/or fully resected surface of the second bone 16. In other embodiments, the coupling surface 406d and/or the lower surface 706 of the shims 700c, 700d includes a patient-specific surface configured to match a surface topography of at least a portion of the second bone 16.

In some embodiments, the first spacer 400d and one or more shims 700c, 700d are configured to fill a joint space between the first bone 14 and the second bone 16 and position the bones 14, 16 in a corrected alignment. In some embodiments, the corrected alignment of the joint 12 corresponds to a preoperatively planned deformity correction that is planned based on anatomic references and/or surgeon preferences. The spacer 400d and the one or more shims 700c, 700d set a varus/valgus and/or flexion/extension relationship between the first bone 14 and the second bone 16 intraoperatively.

Figure 40:
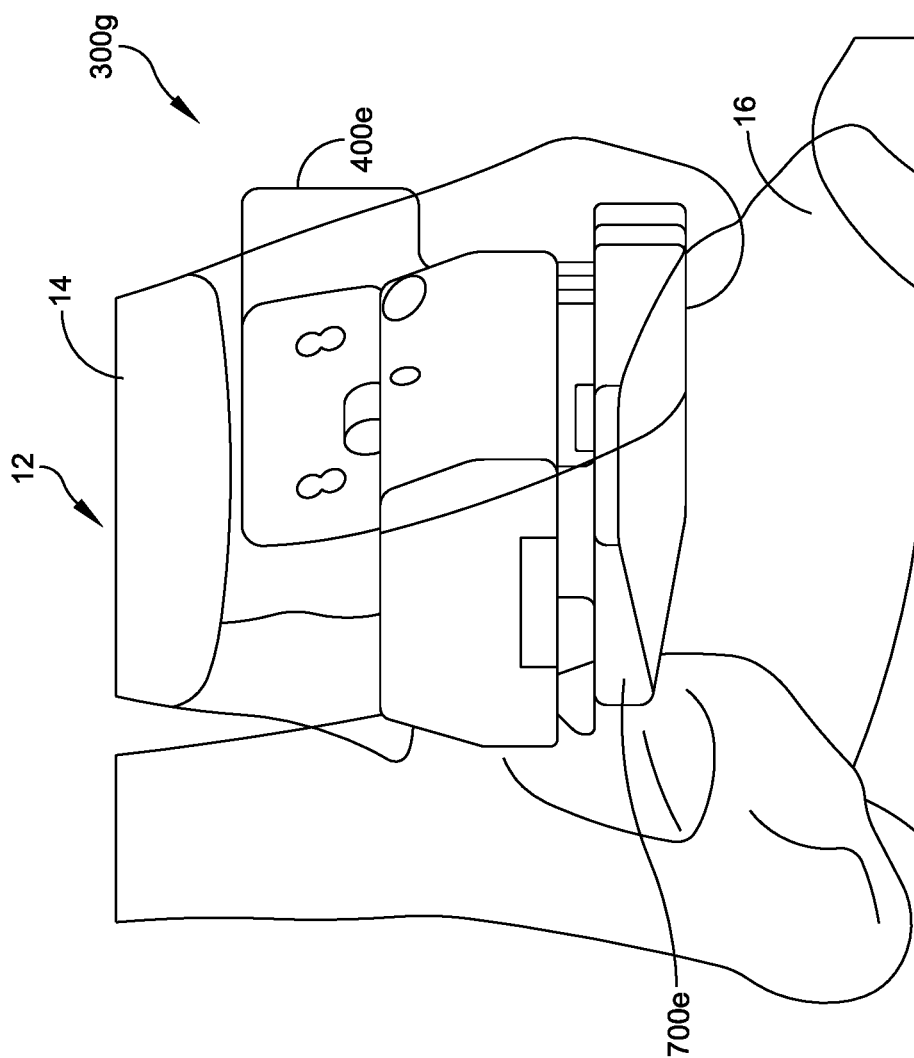
FIG. 40 illustrates an isometric view of a spacer assembly including a first spacer and a fixed angle shim configured to abut a second bone of a joint, in accordance with some embodiments.
Figure 41:
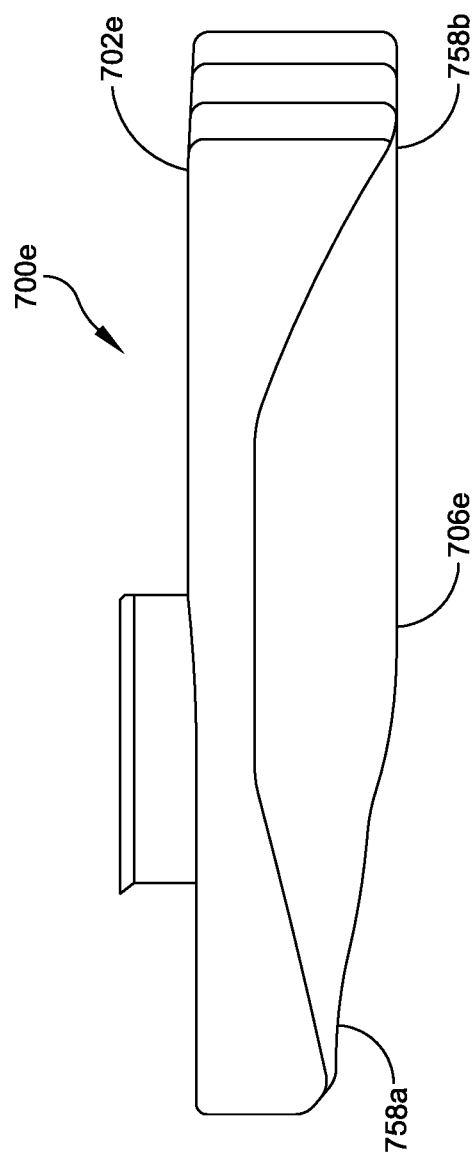
FIG. 41 illustrates the fixed angle shim of FIG. 40, in accordance with some embodiments.

FIGS. 40-41 illustrates a spacer assembly 300g including a first spacer 400e and an angled shim 700e, in accordance with some embodiments. The spacer assembly 300g is similar to the spacer assembly 300f discussed above in conjunction with FIG. 39, and similar description is not repeated herein. The spacer assembly 300g includes an angled shim 700e having a body 702e including one or more angled facets 758a, 758b. The body 702e includes a planar upper surface 704e and a lower surface 706e including a plurality of facets 758a, 758b each extending at an angle with respect to the upper surface 704e. For example, in some embodiments, the lower surface 706e includes a first facet 758a extending at a first angle with respect to the upper surface 704 and a second facet 758b extending at a second angle with respect to the upper surface 704. The first facet 758a and the second facet 758b are perpendicular, although it will be appreciated that the first facet 758a can be positioned at any angle with respect to the second facet 758b. In some embodiments, the lower surface 706e includes a patient-specific profile configured to match a surface profile of the second bone 16.

In some embodiments, the body 702e of the shim 700e is configured to abut a second bone 16. The shim 700e and the first spacer 400e are configured to fill a joint space between first bone 14 and second bone 16 and position bones 14, 16 in a corrected alignment. In some embodiments, the corrected alignment of joint 12 corresponds to a preoperatively planned deformity correction that is planned based on anatomic references and/or surgeon preferences. First spacer 400e and shim 700e set one or more degrees of freedom of joint 12. For example, in various embodiments, the spacer assembly 300e can correct one or more of a varus/valgus orientation, a flexion/extension orientation, an inversion/eversion orientation, an anterior/posterior position, a medial/lateral position, and/or a proximal/distal position between the first bone 14 and the second bone 16 intraoperatively.

Figure 42:
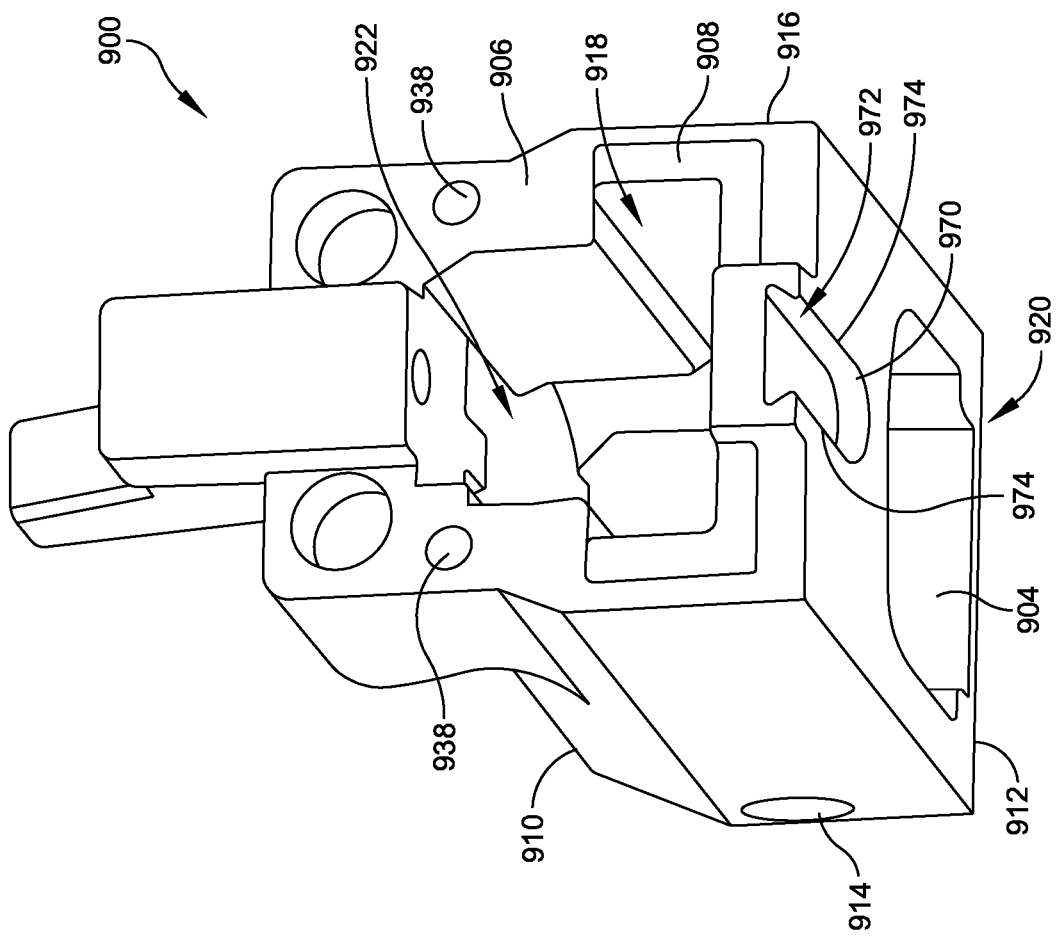
FIG. 42 illustrates a drill guide mount configured to be coupled to at least one shim, in accordance with some embodiments.
Figure 43:
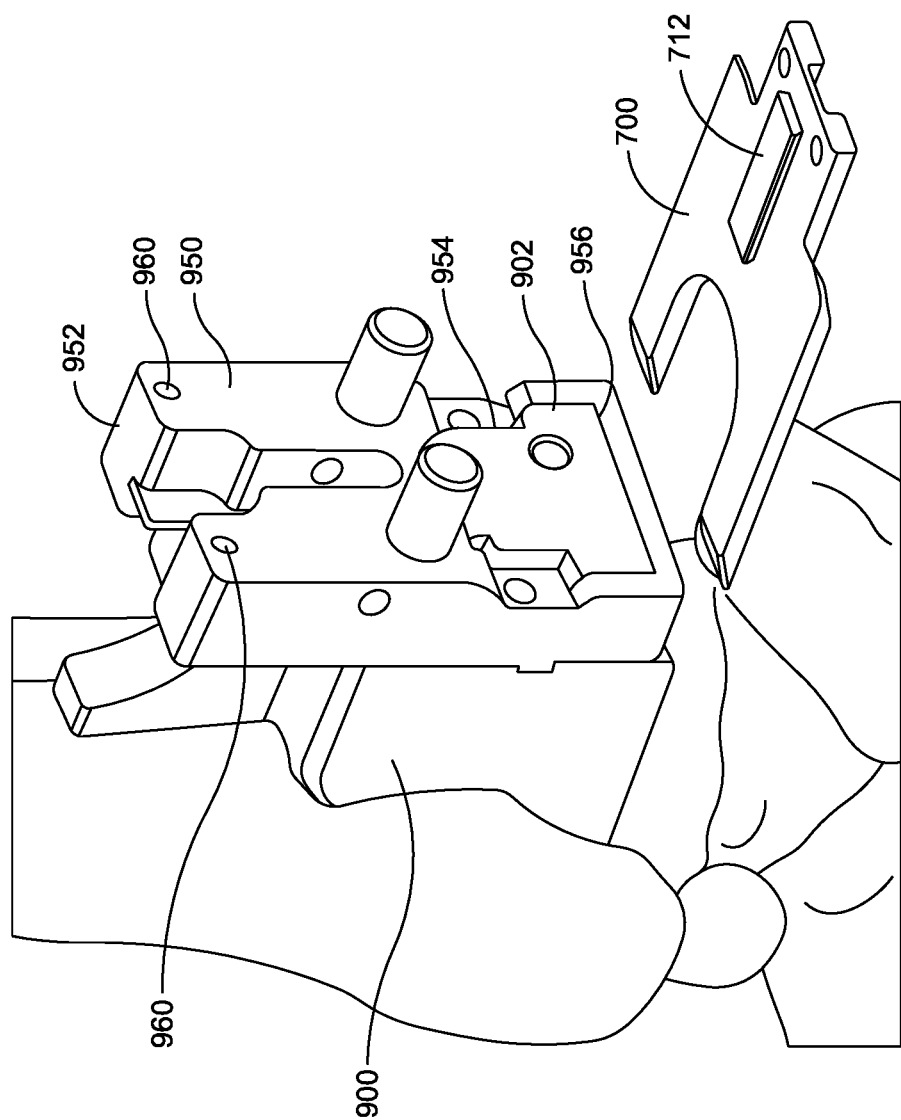
FIG. 43 illustrates the drill guide mount of FIG. 42 coupled to a first bone and a first shim configured to be coupled to the drill guide mount, in accordance with some embodiments.

FIGS. 42-43 illustrate a drill guide mount 900 configured to be inserted into a resected joint 12, in accordance with some embodiments. The drill guide mount 900 is sized and configured to receive a drill guide cartridge 902. The drill guide mount 900 may be manufactured from a resilient polymer material of the type that is suitable for use in connection with stereo lithography, selected laser sintering, or the like manufacturing equipment, e.g., a polyamide powder repaid prototype material is suitable for use in connection with the selective laser sintering.

Drill guide mount 900 has a somewhat rectangular body 904 having a front side 906, a rear side 908, top side 910, bottom side 912, and a pair of opposed sides 914 and 916. Front side 906 defines a recess 918 sized and configured to slideably receive tibial drill guide 902 therein. Recess 918 communicates with a recess 920 defined by bottom side 912 and a recess 922 defined by top side 910 such that body 904 is substantially hollow. Tibial drill guide cartridge 902 has a substantially rectangular elongate body 954 that may be formed from a more substantial material than tibial drill guide mount 900 such as, for example, metals, ceramics, or the like. The geometry of the sides of tibial drill guide cartridge 902 are respectively complementary to the sides 914, 916 of tibial drill guide mount 700.

A mounting plate 950, as best seen in FIG. 43, has a substantially rectangular body 952 that is fabricated from a material including, but not limited to, metals, ceramics, or other suitably rigid and durable material. Body 952 defines an aperture 954 the extends from a front side to a back side and has a similar geometry of recess 918 of drill guide mount 900 such that drill guide cartridge 902 may be received therein. Body 952 also defines a pair of through holes 960 that are arranged on body 952 such that they correspond to holes 938 of tibial drill guide mount 700 and are sized and configured to receive a k-wire or pin therein. Additional description of a tibial drill guide mount can be found in U.S. Pat. No. 8,808,303, which is incorporated by reference herein in its entirety.

Referring again to FIG. 42, bottom side 912 of drill guide mount 900 includes a dovetail joint 970. Dovetail joint 970 has a similar construction to the dovetail joint 440 described above with respect to the first spacer 400. A cavity 972 is defined in bottom side 912 between rails 974. Cavity 972 is sized and configured to receive a corresponding dovetail extension 712 extending from a shim 700. Although embodiments are discussed herein including a dovetail joint 970, it will be appreciated that bottom side 912 can define any suitable cavity sized and configured to couple to extension 712 defined by the shim 700.

Shim 700 is configured to provide stability for the tibia drill guide mount 900 and the second bone 16. For example, one or more shims 700 can be coupled to bottom side 912 fill a space between bottom side 912 and a top surface of resected second bone 16. In some embodiments, shims 700 are identical to shims used to correct laxity between a first spacer 400 and a second spacer 500. In other embodiments, one or more shims 700 configured to couple to tibial drill guide mount 900 can have a different profile, different thickness, etc. from the shims positioned between first spacer 400 and second spacer 500.

In some embodiments, once one or more revision cuts are formed in joint 12, for example using the spacer assembly 300 and adjustable guide 600 discussed above, first bone 14 is prepared for a subsequent drilling operation by inserting the drill guide mount 900 into the resected bone space in first bone 14. The drill guide mount 900 and method of drill of first bone 14 are similar to the use of a drill guide as described in U.S. Pat. Appl. Pub. 2015/0257899, which is incorporated by reference herein in its entirety. The drill guide 900 is similar to the drill guide described in U.S. Pat. Appl. Pub. 2015/0257899, but includes a dovetail joint 970 for receiving a portion of a shim 700 therein.

The disclosed system and method advantageously utilize custom manufactured surgical instruments, guides, and/or fixtures that are based upon a patient's anatomy to reduce the use of fluoroscopy during a surgical procedure. In some instances, the use of fluoroscopy during a surgical procedure is eliminated altogether. The custom instruments, guides, and/or fixtures are created by imaging a patient's anatomy with a computer tomography scanner ("CT"), a magnetic resonance imaging machine ("MRI"), or like medical imaging technology prior to surgery and utilizing these images to create patient-specific instruments, guides, and/or fixtures.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A system, comprising:
 a first spacer sized and configured to be received within a joint space of a first bone, the first spacer defining (i) a body extending between a first surface and a second surface and (ii) a slot; and an adjustable guide comprising a guide adapter and a guide body, wherein the guide adapter comprises a flat body, having at least one leaf-spring, and configured to couple the adjustable guide to the first spacer, and wherein the guide body is adjustable along a first axis with respect to the guide adapter and the slot is sized and configured to receive the flat body at least partially therein.

2. The system of claim 1, wherein the guide body comprises a first leg and a second leg extending from the guide body on the first axis and spaced apart to define a slot sized and configured to receive a coupling element extending from the guide adapter.

3. The system of claim 2, comprising a locking element configured to be received on the coupling element to apply a locking force to the first and second legs of the guide body.

4. The system of claim 3, wherein the locking element includes one or more compression features.

5. The system of claim 3, wherein the coupling element defines an external thread and the locking element defines a channel having an internal thread.

6. The system of claim 1, wherein the guide body defines a resection slot.

7. The system of claim 1, wherein the guide body defines at least one hole extending through the guide body and configured to position a guide element in one of the first bone or the second bone.

8. A system, comprising:
a first spacer sized and configured to be received within a joint space of a first bone, the first spacer defining a body extending between a first surface and a second surface;
at least one shim comprising a body extending between an upper surface and a lower surface, wherein the upper surface is configured to couple the at least one shim to the second surface of the first spacer; and
an adjustable guide comprising a guide adapter configured to be coupled the first spacer and a guide body, wherein the guide body comprises a first leg and a second leg extending from the guide body and spaced apart to define a slot sized and configured to receive a biasable coupling element extending from the guide adapter, and wherein the guide body is adjustable along a first axis with respect to the guide adapter.

9. The system of claim 8, wherein the guide body defines at least one hole extending through the guide body and configured to position a guide element in one of the first bone or the second bone.

10. The system of claim 8, wherein the guide adapter comprises a flat body including at least one leaf-spring and the first spacer defines a complementary slot sized and configured to receive the flat body therein.

11. The system of claim 8, comprising a locking element configured to selectively lock the guide body at a selected position on the first axis.

12. A method, comprising:
coupling a first spacer to a joint space of a first bone, the first spacer defining a body extending between a first surface and a second surface, wherein the first surface is positioned in contact with the first bone;
coupling a second spacer to a second bone, the second spacer defining a body extending between a first surface and a second surface, wherein the second surface of the first spacer is configured to abut the second surface of the second spacer to position the first bone and the second bone in a predetermined alignment;
coupling an adjustable guide to one of the first spacer or the second spacer;
adjusting a guide body of the adjustable guide to a first position on a first axis corresponding to a selected depth of a resection cut to be formed in one of the first bone or the second bone;
coupling a guide element to one of the first bone or the second bone by inserting the guide element through a guide hole formed in the guide body of the adjustable guide;
removing the first spacer, the second spacer, and the adjustable guide from the first bone and the second bone;
coupling the guide body of the adjustable guide to the guide element; and
forming a resection cut in one of the first bone or the second bone through a resection slot defined by the guide body.

13. The method of claim 12, wherein adjusting the guide body comprises:
sliding a coupling element extending from a guide adapter of the adjustable guide within a slot defined by a first leg and a second leg extending from the guide body, wherein the slot extends on the first axis; and
coupling a locking element to the coupling element to maintain the coupling element in a selected position within the slot defined by the guide body.

14. The method of claim 13, wherein the locking element is coupled to the coupling element by a threaded engagement.

15. The method of claim 12, comprising inserting a flat extension of the adjustable guide into a slot defined by the one of the first spacer or the second spacer.

16. The method of claim 15, wherein the flat extension defines one or more leaf-spring elements configured to maintain the flat extension within the slot defined by the one of the first spacer or the second spacer.

* * * * *